United States Patent [19]

Deby et al.

[11] Patent Number: 5,460,961
[45] Date of Patent: Oct. 24, 1995

[54] HUMAN MYELOPEROXIDASE AND ITS THERAPEUTIC APPLICATION

[75] Inventors: Carol Deby, Liege; Joel Pincemail, Hony-Esneux; Alex Bollen, Itterbeek, all of Belgium

[73] Assignee: La Region Wallonne, Brussels, Belgium

[21] Appl. No.: 641,678

[22] Filed: Jan. 16, 1991

Related U.S. Application Data

[63] Continuation-in-part of Ser. No. 460,931, Feb. 14, 1990, abandoned.

[30] Foreign Application Priority Data

Jun. 14, 1988 [FR] France .................................. 88 07914

[51] Int. Cl.$^6$ .............. C12N 9/08; C12N 15/53; A61K 37/50; A01N 25/28
[52] U.S. Cl. ................. 435/192; 435/69.1; 435/189; 435/252.3; 435/520.1; 435/14; 435/32; 435/66; 435/70; 424/94.4; 424/417; 424/418; 536/23.2
[58] Field of Search ................ 435/192, 69.1, 435/252.3, 252.33, 320.1, 189; 530/391.7; 536/23.2

[56] References Cited

U.S. PATENT DOCUMENTS

| | | | |
|---|---|---|---|
| 4,306,025 | 12/1981 | Aasegawa et al. | 435/192 |
| 4,379,141 | 4/1983 | Aasegawa et al. | 424/94 |
| 4,894,443 | 1/1990 | Greenfield et al. | 530/388 |
| 4,943,527 | 7/1990 | Protter et al. | 435/96.6 |
| 5,049,493 | 9/1991 | Khosla et al. | 435/69.1 |
| 5,059,528 | 10/1991 | Bollen et al. | 435/69.4 |
| 5,240,831 | 8/1993 | Barnes | 435/69.1 |

FOREIGN PATENT DOCUMENTS

| | | | |
|---|---|---|---|
| 0098073 | 1/1984 | European Pat. Off. | 424/94 |
| 0336379 | 10/1989 | European Pat. Off. | 530/387 |
| 2108387 | 5/1983 | United Kingdom | 435/192 |

OTHER PUBLICATIONS

Johnson, K. R., et al., 1987, Nucleic Acids Research, 15(5): 2013–2028.
Hashinaka, K., et al., 1988, Biochemistry 27: 5906–5914.
Weil, S. C., et al., 1987, Proceedings of The National Academy of Sciences, U.S.A., 84: 2057–2061.
Morishita, K., et al., 1987, Journal of Biological Chemistry 262(8): 3844–3851; 262(31): 15208–15213.
Yamada, M., et al., 1987, Archives of Biochemistry and Biophysics, 255(1): 147–155.
Tournay, C., et al., 1993, Antimicrobial Agents and Chemotherapy 37(1).
Moguilevsky, N., et al., 1992 FEBS Letters, 302(3): 209–212.

*Primary Examiner*—Robert A. Wax
*Assistant Examiner*—William W. Moore
*Attorney, Agent, or Firm*—Pollock, Vande Sande & Priddy

[57] ABSTRACT

A substantially pure recombinant human myeloperoxidase heme-containing precursor, comprising a glycoprotein of 84 KD with the amino acid sequence coded for by the nucleotide sequence from 145 to 2235 corresponding to codons 49 to 745 in phase after the first methionine codon in FIG. 1 produced by culturing prokaryotic or eukaryotic cells transformed by a vector for the expression of human myeloperoxidase precursor in said cells.

13 Claims, 16 Drawing Sheets

```
Hind III                            Nsi I
------    Met                       ------
   AGCTTACCATGGGGGTTCCCTTCTTCTCTTCTCTCAGATGCATGGTGGACTTAGGACCTTGCTGGGCTGGGGGTCTCAC

TGCAGAGATGAAGCTGCTTCTGGCCCTAGCAGGCGTCCTGGCCATTCTGGCCACGCCCCAGCCCTCTGAAGGTGCTGCTC

CAGCTGTCCTGGGGGAGGTGGACACCTCGTTGGTGCTGAGCTCCATGGAGGAGGCCAAGCAGCTGGTGGACAAGGCCTAC

AAGGAGCGGCGGGAAAGCATCAAGCAGCGGCTTCGCAGCGGCTCAGCCAGCCCCATGGAACTCCTATCCTACTTCAAGCA

GCCGGTGGCAGCCACCAGGACGGCGGTGAGGGCCGCTGACTACCTGCACGTGGCTCTAGACCTGCTGGAGAGGAAGCTGC
                                                       Xba I
GGTCCCTGTGGCGAAGGCCATTCAATGTCACTGATGTGCTGACGCCCGCCCAGCTGAATGTGTTGTCCAAGTCAAGCGGC

TGCGCCTACCAGGACGTGGGGGTGACTTGCCCGGAGCAGGACAAATACCGCACCATCACCGGGATGTGCAACAACAGACG

CAGCCCCACGCTGGGGGCCTCCAACCGTGCCTTTGTGCGCTGGCTGCCGGCGGAGTATGAGGACGGCTTCTCTCTTCCCT

ACGGCTGGACGCCCGGGGTCAAGCGCAACGGCTTCCCGGTGGCTCTGGCTCGCGCGGTCTCCAACGAGATCGTGCGCTTC

CCCACTGATCAGCTGACTCCGGACCAGGAGCGCTCACTCATGTTCATGCAATGGGGCCAGCTGTTGGACCACGACCTCGA

CTTCACCCCTGAGCCGGCCGCCCGGGCCTCCTTCGTCACTGGCGTCAACTGCGAGACCAGCTGCGTTCAGCAGCCGCCCT

GCTTCCCGCTCAAGATCCCGCCCAATGACCCCCGCATCAAGAACCAAGCCGACTGCATCCCGTTCTTCCGCTCCTGCCCG

GCTTGCCCCGGGAGCAACATCACCATCCGCAACCAGATCAACGCGCTCACTTCCTTCGTGGACGCCAGCATGGTGTACGG

CAGCGAGGAGCCCCTGGCCAGGAACCTGCGCAACATGTCCAACCAGCTGGGGCTGCTGGCCGTCAACCAGCGCTTCCAAG

ACAACGGCCGGGCCCTGCTGCCCTTTGACAACCTGCACGATGACCCCTGTCTCCTCACCAACCGCTCAGCGCGCATCCCC

TGCTTCCTGGCAGGGGACACCCGTTCCAGTGAGATGCCCGAGCTCACCTCCATGCACACCCTCTTACTTCGGGAGCACAA

CCGGCTGGCCACAGAGCTCAAGAGCCTGAACCCTAGGTGGGATGGGGAGAGGCTCTACCAGGAAGCCCGGAAGATCGTGG

GGGCCATGGTCCAGATCATCACTTACCGGGACTACCTGCCCCTGGTGCTGGGGCCAACGGCCATGAGGAAGTACCTGCCC

ACGTACCGTTCCTACAATGACTCAGTGGACCCACGCATCGCCAACGTCTTCACCAATGCCTTCCGCTACGGCCACACCCT

CATCCAACCCTTCATGTTCCGCCTGGACAATCGGTACCAGCCCATGGAACCGAACCCCCGTGTCCCCCTCAGCAGGGTCT

TTTTTGCCTCCTGGAGGGTCGTGCTGGAAGGTGGCATTGACCCCATCCTCCGGGGCCTCATGGCCACCCCTGCCAAGCTG

AATCGTCAGAACCAAATTGCAGTGGATGAGATCCGGGAGCGATTGTTTGAGCAGGTCATGAGGATTGGGCTGGACCTGCC

TGCTCTGAACATGCAGCGCAGCAGGGACCACGGCCTCCCAGGATACAATGCCTGGAGGCGCTTCTGTGGGCTCCCGCAGC

CTGAAACTGTGGGCCAGCTGGGCACGGTGCTGAGGAACCTGAAATTGGCGAGGAAACTGATGGAGCAGTATGGCACGCCC

AACAACATCGACATCTGGATGGGCGGCGTGTCCGAGCCTCTGAAGCGCAAAGGCCGCGTGGGCCCACTCCTCGCCTGCAT

CATCGGTACCCAGTTCAGGAAGCTCCGGGATGGTGATCGGTTTTGGTGGGAGAACGAGGGTGTGTTCAGCATGCAGCAGC

GACAGGCCCTGGCCCAGATCTCATTGCCCCGGATCATCTGCGACAACACAGGCATCACCACCGTGTCTAAGAACAACATC
                 Bgl II
TTCATGTCCAACTCATATCCCCGGGACTTTGTCAACTGCAGTACACTTCCTGCATTGAACCTGGCTTCCTGGAGGGAAGC
                                     ------
CTCCTGATATCTACGTATGGTT          Pst I
***.   ------ ------
------SnaB I  Hpa I
EcoR V
```

FIG.1

FIG_4

O.D. at 410nm for 0 ng/ml : 0,016

Vector pAcYM1

FIG_6
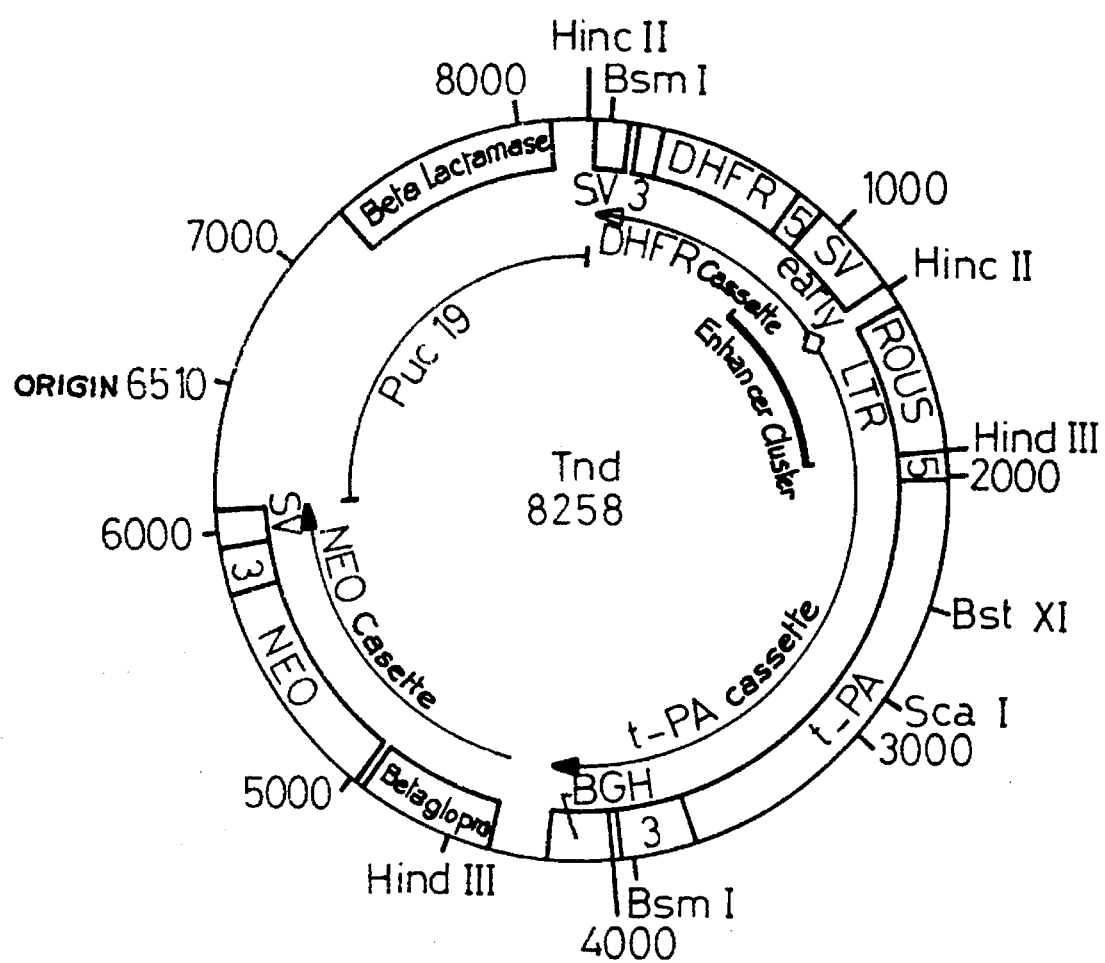

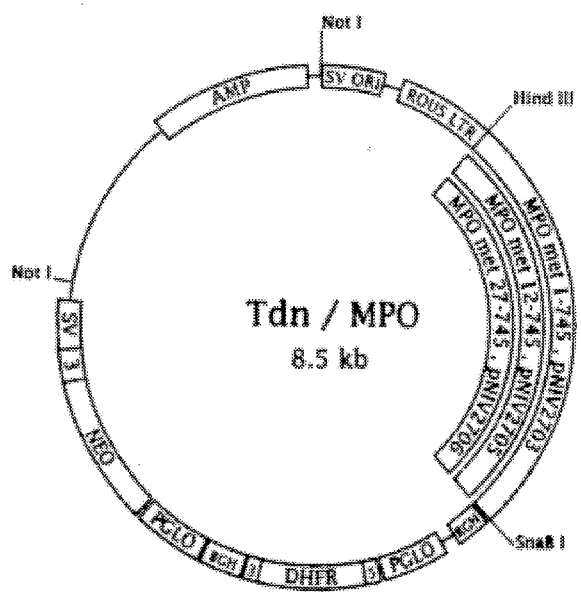
FIG._7
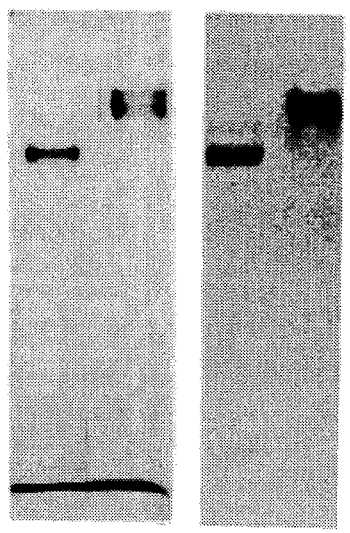
FIG._8

```
                    50                    55
       Glu Gly Ala Ala Pro Ala Val Leu Gly Glu 60             65
       Val (Asp) Thr (Ser) Leu Val Leu Ser Ser
```

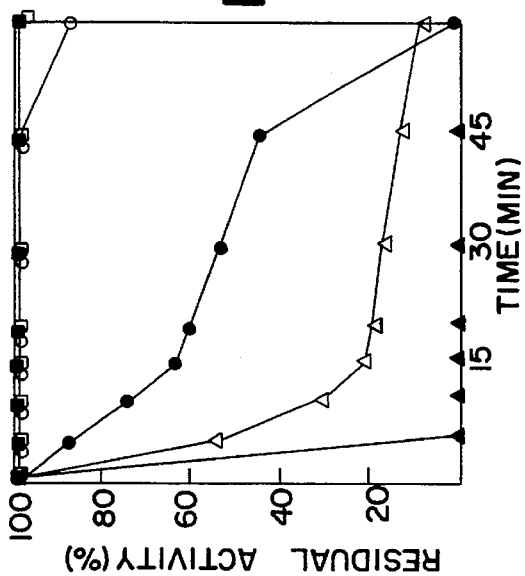
FIG.IIB
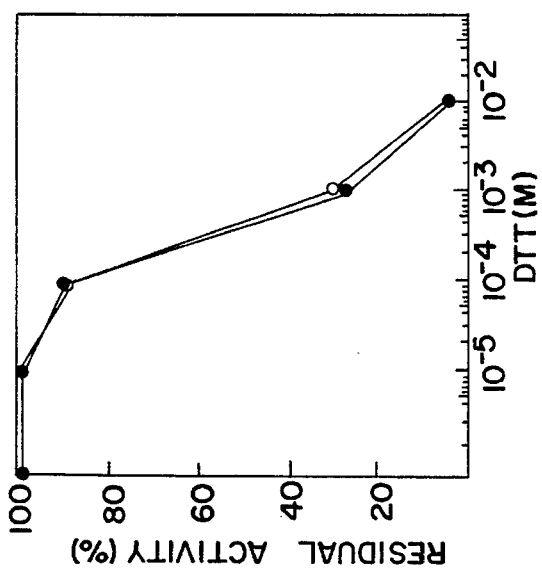
FIG.IID
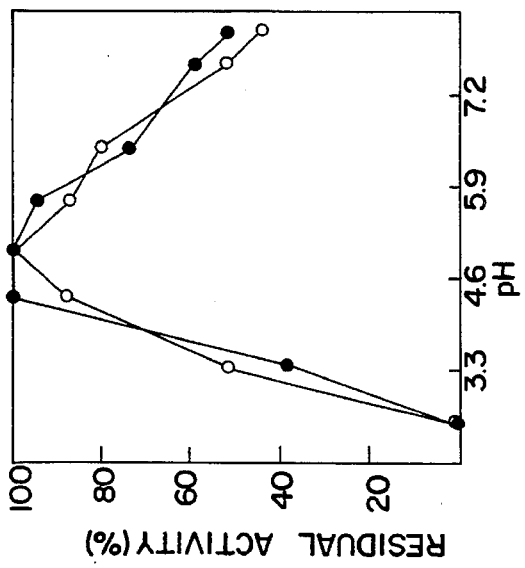
FIG.IIA
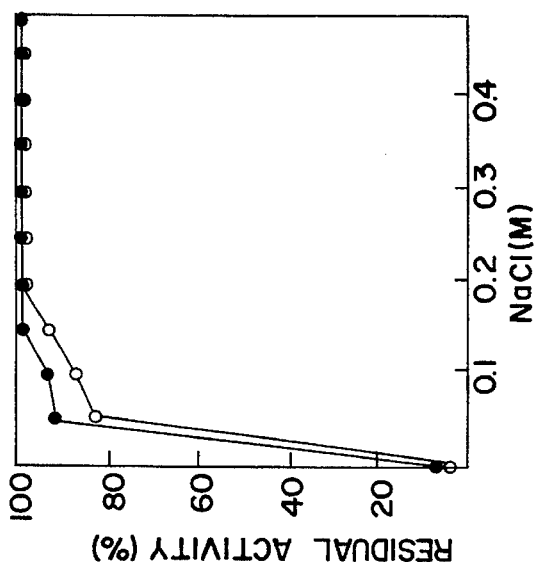
FIG.IIC

```
GCT GCT CCA GCT GTC CTG GGG GAG GTG GAC ACC TCG TTG GTG CTG AGC TCC ATG GAG GAG
Ala Ala Pro Ala Val Leu Gly Glu Val Asp Thr Ser Leu Val Leu Ser Ser Met Glu Glu
49                                          60

GCC AAG CAG CTG GTG GAC AAG GCC TAC AAG GAG CGG CGG GAA AGC ATC AAG CAG CGG CTT
Ala Lys Gln Leu Val Asp Lys Ala Tyr Lys Glu Arg Arg Glu Ser Ile Lys Gln Arg Leu
                                            80

CGC AGC GGC TCA GCC AGC CCC ATG GAA CTC CTA TCC TAC TTC AAG CAG CCG GTG GCA GCC
Arg Ser Gly Ser Ala Ser Pro Met Glu Leu Leu Ser Tyr Phe Lys Gln Pro Val Ala Ala
                                            100

ACC AGG ACG GCG GTG AGG GCC GCT GAC TAC CTG CAC GTG GCT CTA GAC CTG GAG AGG CTT
Thr Arg Thr Ala Val Arg Ala Ala Asp Tyr Leu His Val Ala Leu Asp Leu Glu Arg
                                            120

AAG CTG CGG TCC CTG TGG CGA AGG CCA TTC AAT GTC ACT GAT GTG CTG ACG CCC GCC CAG
Lys Leu Arg Ser Leu Trp Arg Arg Pro Phe Asn Val Thr Asp Val Leu Thr Pro Ala Gln
                                            140

CTG AAT GTG TTG TCC AAG TCA AGC GGC TGC GCC TAC CAG GAC GTG GGG GTG ACT TGC CCG
Leu Asn Val Leu Ser Lys Ser Ser Gly Cys Ala Tyr Gln Asp Val Gly Val Thr Cys Pro
                                            160
```

FIG. 15A

```
GAG CAG GAC AAA TAC CGC ACC ATC ACC GGG ATG TGC AAC AAC AGA CGC AGC CCC ACG CTG
Glu Gln Asp Lys Tyr Arg Thr Ile Thr Gly Met Cys Asn Asn Arg Arg Ser Pro Thr Leu
                                            180

GGG GCC TCC AAC CGT GCC TTT GTG CGC TGG CTG CCG GCG GAG TAT GAG GAC GGC TTC TCT
Gly Ala Ser Asn Arg Ala Phe Val Arg Trp Leu Pro Ala Glu Tyr Glu Asp Gly Phe Ser
                                            200

CTT CCC TAC GGC TGG ACG CCC GGG GTC AAG CGC AAC GGC TTC CCG GTG GCT CTG GCT CGC
Leu Pro Tyr Gly Trp Thr Pro Gly Val Lys Arg Asn Gly Phe Pro Val Ala Leu Ala Arg
                                            220

GCG GTC TCC AAC GAG ATC GTG CGC TTC CCC ACT GAT CAG CTG ACT CCG GAC CAG GAG CGC
Ala Val Ser Asn Glu Ile Val Arg Phe Pro Thr Asp Gln Leu Thr Pro Asp Gln Glu Arg
                                            240

TCA CTC ATG TTC ATG CAA TGG GGC CAG CTG TTG GAC CAC CTC GAC TTC ACC CCT GAG
Ser Leu Met Phe Met Gln Trp Gly Gln Leu Leu Asp His Asp Leu Asp Phe Thr Pro Glu
                                            260

CCG GCC CGG GCC TCC TTC GTC ACT GGC GTC AAC TGC GAG ACC AGC TGC GTT CAG CAG
Pro Ala Arg Ala Ser Phe Val Thr Gly Val Asn Cys Glu Thr Ser Cys Val Gln Gln
                                            280
```

```
CCG CCC TGC TTC CCG CTC AAG ATC CCG CCC AAT GAC CCC CGC ATC AAG AAC CAA GCC GAC
Pro Pro Cys Phe Pro Leu Lys Ile Pro Pro Asn Asp Pro Arg Ile Lys Asn Gln Ala Asp
                                        300

TGC ATC CCG TTC TTC CGC TCC TGC CCG GCT TGC CCC GGG AGC AAC ATC ACC ATC CGC AAC
Cys Ile Pro Phe Phe Arg Ser Cys Pro Ala Cys Pro Gly Ser Asn Ile Thr Ile Arg Asn
                                        320

CAG ATC AAC GCG CTC ACT TCC TTC GTG GAC GCC AGC ATG GTG TAC GGC AGC GAG GAG CCC
Gln Ile Asn Ala Leu Thr Ser Phe Val Asp Ala Ser Met Val Tyr Gly Ser Glu Glu Pro
                                        340

CTG GCC AGG AAC CTG CGC AAC ATG TCC AAC CAG GGG CTG CTG GCC GTC AAC CAG CGC
Leu Ala Arg Asn Leu Arg Asn Met Ser Asn Gln Gly Leu Leu Ala Val Asn Gln Arg
                                        360

TTC CAA GAC AAC GGC CGG GCC CTG CTG CCC TTT GAC AAC CTG CAC GAT GAC CCC TGT CTC
Phe Gln Asp Asn Gly Arg Ala Leu Leu Pro Phe Asp Asn Leu His Asp Asp Pro Cys Leu
                                        380

CTC ACC AAC CGC TCA GCG CGC ATC CCC TGC TTC CTG GCA GGG GAC ACC CGT TCC AGT GAG
Leu Thr Asn Arg Ser Ala Arg Ile Pro Cys Phe Leu Ala Gly Asp Thr Arg Ser Ser Glu
                                        400
```

```
ATG CCC GAG CTC ACC TCC ATG CAC ACC CTC TTA CTT CGG GAG CAC AAC CGG CTG GCC ACA
Met Pro Glu Leu Thr Ser Met His Thr Leu Leu Leu Arg Glu His Asn Arg Leu Ala Thr
                                              420

GAG CTC AAG AGC CTG AAC CCT AGG TGG GAT GGG GAG AGG CTC TAC CAG GAA GCC CGG AAG
Glu Leu Lys Ser Leu Asn Pro Arg Trp Asp Gly Glu Arg Leu Tyr Gln Glu Ala Arg Lys
                                              440

ATC GTG GGG GCC ATG GTC CAG ATC ACT TAC CGG GAC TAC CTG CCC CTG GTG CTG GGG
Ile Val Gly Ala Met Val Gln Ile Ile Thr Tyr Arg Asp Tyr Leu Pro Leu Val Leu Gly
                                              460

CCA ACG GCC ATG AGG AAG TAC CTG CCC ACG TAC CGT TCC TAC AAT GAC TCA GTG GAC CCA
Pro Thr Ala Met Arg Lys Tyr Leu Pro Thr Tyr Arg Ser Tyr Asn Asp Ser Val Asp Pro
                                              480

CGC ATC GCC AAC GTC TTC ACC AAT GCC TTC CGC CAC ACC GGC TAC CTC ATC CAA CCC TTC
Arg Ile Ala Asn Val Phe Thr Asn Ala Phe Arg His Thr Gly Tyr Leu Ile Gln Pro Phe
                                              500

ATG TTC CGC CTG GAC AAT CGG TAC CAG CCC ATG GAA CCC AAC CCC CGT GTC CCC CTC AGC
Met Phe Arg Leu Asp Asn Arg Tyr Gln Pro Met Glu Pro Asn Pro Arg Val Pro Leu Ser
                                              520
```

FIG. 15D

```
AGG GTC TTT TTT GCC TCC TGG AGG GTC GTG CTG GAA GGT GGC ATT GAC CCC ATC CTC CGG
Arg Val Phe Phe Ala Ser Trp Arg Val Val Leu Glu Gly Gly Ile Asp Pro Ile Leu Arg
                                            540

GGC CTC ATG GCC ACC CCT GCC AAG CTG AAT CGT CAG AAC CAA ATT GCA GTG GAT GAG ATC
Gly Leu Met Ala Thr Pro Ala Lys Leu Asn Arg Gln Asn Gln Ile Ala Val Asp Glu Ile
                                            560

CGG GAG CGA TTG TTT GAG CAG GTC ATG AGG ATT GGG ATC CTG GAC CCT GCT CTG AAC ATG
Arg Glu Arg Leu Phe Glu Gln Val Met Arg Ile Gly Ile Leu Asp Pro Ala Leu Asn Met
                                            580

CAG CGC AGC AGG GAC CAC GGC CTC CCA GGA TAC AAT GCC TGG AGG CGC TTC TGT GGG CTC
Gln Arg Ser Arg Asp His Gly Leu Pro Gly Tyr Asn Ala Trp Arg Arg Phe Cys Gly Leu
                                            600

CCG CAG CCT GAA ACT GTG GGC CAG CTG GGC ACG GTG CTG AGG AAC CTG AAA TTG GCG AGG
Pro Gln Pro Glu Thr Val Gly Gln Leu Gly Thr Val Leu Arg Asn Leu Lys Leu Ala Arg
                                            620

AAA CTG ATG GAG CAG TAT GGC ACG CCC AAC AAC ATC GAC ATC TGG ATG GGC GGC GTG TCC
Lys Leu Met Glu Gln Tyr Gly Thr Pro Asn Asn Ile Asp Ile Trp Met Gly Gly Val Ser
                                            640
```

FIG.15E

```
GAG CCT CTG AAG CGC AAA GGC CGC GTG GGC CCA CTC CTC GCC TGC ATC ATC GGT ACC CAG
Glu Pro Leu Lys Arg Lys Gly Arg Val Gly Pro Leu Leu Ala Cys Ile Ile Gly Thr Gln
                                                    660

TTC AGG AAG CTC CGG GAT GGT GAT CGG TTT TGG GAG AAC GAG GGT GTG TTC AGC ATG
Phe Arg Lys Leu Arg Asp Gly Asp Arg Phe Trp Glu Asn Glu Gly Val Phe Ser Met
                                            680

CAG CGA CAG GCC CTG GCC CAG ATC TCA TTG CCC CGG ATC ATC TGC GAC AAC ACA GGC
Gln Arg Gln Ala Leu Ala Gln Ile Ser Leu Pro Arg Ile Ile Cys Asp Asn Thr Gly
                                                    700

ATC ACC ACC GTG TCT AAG AAC AAC ATC TTC ATG TCC AAC TCA TAT CCC CGG GAC TTT GTC
Ile Thr Thr Val Ser Lys Asn Asn Ile Phe Met Ser Asn Ser Tyr Pro Arg Asp Phe Val
                                                720

AAC TGC AGT ACA CTT CCT GCA TTG AAC CTG GCT TCC TGG AGG GAA GCC TCC TGA
Asn Cys Ser Thr Leu Pro Ala Leu Asn Leu Ala Ser Trp Arg Glu Ala Ser ***
                                        740
```

FIG.15F

HUMAN MYELOPEROXIDASE AND ITS THERAPEUTIC APPLICATION

The instant application, Ser. No. 07/641,678, filed Jan. 16, 1991, is a Continuation-in-Part of the parent application, Ser. No. 07/460,931, filed Feb. 14, 1990, and now abandoned.

FIELD OF THE INVENTION

The present invention relates to the enzyme human myeloperoxidase (hMPO), to its preparation by genetic engineering and to its use by way of a medicinal product. It hence also relates to its use for the manufacture of pharmaceutical compositions containing it, as well as to the pharmaceutical compositions themselves.

More specifically, the therapeutic application in question relates to the treatment of immunodeficient patients in human therapy, by the reinforcement of antimicrobial activity at macrophage level, this applying in all cases of immune deficiencies whether caused, in particular, by AIDS, burns or irradiation.

BACKGROUND OF THE INVENTION

Resistance to infection by microorganisms makes use of non-specific functions (enzyme action, pH, epithelial wall) and of the adaptive immune responses of B and T lymphocytic cells.

The non-specific functions prevent invasion by the majority of attacking agents. However, when this first line of defense capitulates, the phagocytic-system comes into operation, destroys the infectious agents and stimulates the immunity functions conferred by the B and T cells.

Any abnormality, hereditary or acquired, of the phagocytic system has serious consequences, since even microorganisms which are normally of low pathogenicity evade it and trigger recurrent infections.

Moreover, any deficiency in the immune system itself, at T or B cell level, leads to an enhanced susceptibility to intra- or extracellular viral and bacterial infections. These deficiencies may be hereditary or acquired (e.g. AIDS=elective T cell deficiency). Most people suffering from these deficiencies are subject to infection by opportunistic organisms (bacteria, protozoa, and the like).

In all cases of immunosuppression, it is hence desirable that the phagocytic system is as effective as possible, in order to limit the consequences of external attack. Of secondary importance under normal conditions, phagocytosis takes on an essential character when the B and T immune response weakens.

Among cells associated with the immune response, the polymorphonuclear leukocytes are of special interest in the context of combating infections. These cells contain an enzyme, myeloperoxidase, whose microbicidal action is well documented. Polynuclear cells do not display any specificity with respect to an antigen, but play an essential part in the case of acute inflammation, with antibodies and the complement system, in the host's defense against microorganisms. Their main function is phagocytosis. During this process, the microorganisms are included in vacuoles (phagosomes) which fuse with the granules containing myeloperoxidase to form phagolysosomes. During phagocytosis, the enzymatic activity of the myeloperoxidase leads to the formation of HOCl, a potent bactericidal compound (hypochlorous acid); this activity requires $H_2O_2$ (hydrogen peroxide), which appears in the polymorphonuclear cell when it is stimulated by various agents, and in particular by the immunological reactions induced by microorganisms. Hypochlorous acid is oxidizing in itself, but produces still more strongly oxidizing derivatives, chloramines. Finally, reacting with $H_2O_2$ from which it is derived, hypochlorous acid produces an extremely oxidizing form of oxygen, singlet oxygen.

SUMMARY OF THE INVENTION

The major problem nevertheless lies at macrophage level. In effect, the macrophage is a very large cell, more robust than the polymorphonuclear cell and capable, like the latter, of phagocytosing microorganisms. It also possesses an $H_2O_2$-generating system but is not, however, capable of producing myeloperoxidase. This deficiency decreases its defensive efficacy. It has been discovered, however, according to the invention, that macrophages can incorporate and utilize myeloperoxidase, which remains active after penetration into the macrophages, an acquisition complementing in an effective manner their cytolytic and bacteriolytic arsenal, especially for the destruction of various infectious agents affecting immunosuppressed patients.

Although myeloperoxidase, once in the plasma, is taken up very quickly by the macrophages, specific administration systems-delivering the enzyme in an optimal manner to the macrophages can be used according to the invention, producing myeloperoxidase conjugates by covalent coupling with a transporting agent possessing an affinity for macrophages. In this connection, there may be mentioned transporting agents such as mannosylated human albumin, as well as antibodies or antibody fragments, such as the Fc constant portion, directed towards receptors present on macrophages.

Other systems consist in coupling an antibody or Ab fragment specific for the macrophage to the enzyme human myeloperoxidase by non-covalent complexing or by DNA manipulation, to obtain an "immune complex".

The administration of such conjugates or immune complexes leads to targeting of the human MPO towards the macrophage, to its ingestion by phagocytosis and to release of the enzyme in active form within the macrophage, its preferential site of action, where it participates in combating infections.

In the case of immune complexes prepared by genetic engineering, DNA coding for MPO, the latter being active or in the form of a natural precursor, is coupled to DNA coding for an immunoglobulin fragment specifically recognizing macrophages.

The subject of the present invention is hence, by way of a medicinal product, a compound consisting of the enzyme human myeloperoxidase.

The subject of the invention is also, by way of a medicinal product, a compound consisting of a myeloperoxidase conjugate, by covalent coupling or complexing with a transporting agent possessing an affinity for macrophages, such as mannosylated human albumin or an antibody or antibody fragments, for example, the Fc constant portion directed towards receptors present on macrophages.

Another compound which is the subject of the present invention, delivering myeloperoxidase in an optimal manner to macrophages, also consists of liposomes, in particular biopolymerized liposomes, in which myeloperoxidase is encapsulated.

The medicinal products according to the invention are useful, in particular, for combating infections within macrophages.

Preferably, the enzyme human myeloperoxidase, used according to the invention, is of recombinant origin, that is to say prepared by genetic engineering.

Furthermore, the subject of the present invention is the use of the compounds according to the invention for the manufacture of pharmaceutical compositions useful, in particular, for the treatment of immunodeficiencies caused, in particular, by AIDS, burns or irradiation.

Finally, the subject of the present invention is pharmaceutical compositions comprising, by way of active principle, the compounds according to the invention.

The pharmaceutical compositions according to the invention may be presented in different forms, suitable for various forms of administration, in particular parenterally, systemically or topically, or by intravenous injection inasmuch as the target macrophages are present not only in the blood but also in other regions of the body.

The pharmaceutical compositions according to the invention then contain, apart from the active principle, pharmaceutically acceptable vehicles for the administration form in question.

Parenteral administration of myeloperoxidase or of compounds according to the invention is very suitable for the various immunosuppressive syndromes.

The decrease or elimination of natural immune barriers favors the appearance of infections due to pathogenic or opportunistic microorganisms.

Deficiencies in the immune system (for example T cell deficiencies, AIDS, irradiation, anticancer chemotherapy, etc.) are often associated with generalized infections (bacteria, mycoses, viral infections, protozoa, etc.) which are very difficult to control with only the existing antibiotic and chemotherapeutic agents. Under these conditions, myeloperoxidase can also be employed systemically in order to reinforce the antiseptic activity of the macrophages during phagocytosis. In effect, the experimental results indicate that macro phages and monocytes have an increased cytolytic and bacteriolytic activity in the presence of the enzyme.

Myeloperoxidase, or a compound according to the invention, may also be administered by topical application on, in particular, torpid ulcers, where the micro vascularization is deficient (varicose ulcer).

For this topical application, the myeloperoxidase will be incorporated, for example, in water-based paste according to a known dermatological formulation. At the time of use, mixing of the myeloperoxidase suspension may be carried out, as required, with:

either dilute hydrogen peroxide solution (concentration 0.3%, for example)

or another enzyme such as xanthine oxidase.

In this case, a $10^{-3}$M concentration of hypoxanthine, and optionally of ammonium chloride, should be added to the myeloperoxidase suspension. This mixture of pastes produces an evolution of HClO and a formation of amine chloride, which is especially effective for the cleansing or torpid wounds.

Other therapeutic indications may be envisaged for topical treatment:

1. The use of myeloperoxidase is advantageous in the prevention and treatment of intercurrent infections during burns caused thermally, chemically or by irradiation.

2. The phagocytic function appears to be deficient during atopic eczema. In this case, local application of the enzyme can have a beneficial stimulant action on the skin monocytes and macrophages.

3. Myeloperoxidase can have an adjuvant role in the treatment of gum infections, both in immunosuppressed subjects and during paradentoses.

According to the invention, the myeloperoxidase may be obtained by analytical purification from polymorphonuclear leukocytes. Nevertheless, advantageously, the enzyme human myeloperoxidase used will be produced by genetic engineering with recombinant DNA technology.

To this end, the essential stages are:

1. Construction of a library of cDNA-clones which is representative of the products synthesized in leukocytic cells and screening of this library with a suitable probe characteristic of human myeloperoxidase. At the end of this operation, a cDNA clone coding for the enzyme is obtained.

2. The myeloperoxidase cDNA then has to be manipulated in order to permit its expression in various host/vector system. A modular construction is mandatory if it is desired to be capable of assessing expression in systems as varied as *E. coli*, yeasts, mammalian cells or insect cells. The production of an active enzyme, correctly assembled and processed, is advantageously carried out in eukaryotic cell systems.

The subject of the present invention is hence also hMPO produced by culturing prokaryotic or eukaryotic cells transformed by a vector for the expression of hMPO in said cells.

Advantageously, the hMPO according to the invention is produced by cultures of higher eukaryotic cells, in particular by insect or mammalian cells.

To this end, the subject of the present invention is:

1. the purified recombinant human myeloperoxidase precursor heme-containing which is a glycoprotein of 84 KD with the amino acid sequence from position 49 to 745 in phase after the first methionine on FIG. 1 produced by culturing prokaryotic or eukaryotic cells transformed by a vector for the expression of hMPO in said cells.

2. the purified recombinant human myeloperoxidase having the amino acid sequence in FIG. 15.

3. the purified recombinant human myeloperoxidase produced by a vector comprising the coding sequence of the rech MPO consisting in the DNA sequence in FIG. 1 starting either at the first ATG, at the second ATG which is the codon in position 12 or the third ATG which is the codon in position 27, these two last ATG being in phase with the first ATG, in FIG. 1 and finishing with the TGA codon in phase in position 745 with respect to the first ATG in FIG. 1.

4. a 2261-bp HindIII-SnaBI, HindIII-EcoRV or HindIII-HpaI expression cassette carrying the coding sequence for hMPO as shown in FIG. 1, as well as plasmid pNIV2702 containing said cassettes, or one of these three same fragments with a deletion consisting in the sequences starting in the first ATG and finishing with the codon before the second or the third ATG in phase with respect to the first one in FIG. 1.

5. a vector for expression in prokaryotic or eukaryotic cells containing said above cassettes, and especially 6. a recombinant transfer plasmid for Baculovirus containing the hMPO cDNA under the control of the polyhedrin promoter, in particular 7. plasmid pNIV2704 of FIG. 5,
8. insect cells, in particular of *Spodoptera frugiperda*, such as Sf9 cells cotransfected by a vector according to the invention with wild-type viral DNA, and in particular cotransfected by plasmid pNIV2704,
9. insect cells, in particular of *Spodoptera frugiperda*, such as Sf9 infected by a recombinant Baculovirus obtained with a vector according to the invention, in particular from plasmid pNIV2704,
10. hMPO produced by culturing insect cells, in particular of *Spodoptera frugiperda*, such as Sf9 modified by a vector for expression in said cells according to the invention,
11. a vector for expression in mammalian cells, in particular CHO cells, containing the HindIII-SnaBI cassette of FIG. 1, or the coding sequences of above items 3) and 4) in particular plasmid pNIV2703, pNIV705, pNIV2706, of FIG. 7
12. mammalian cells, in particular CHO cells, transfected by a vector for expression in said cells according to the invention, in particular by plasmid pNIV2703 and
13. hMPO produced by culturing mammalian cells in particular CHO, transfected by a vector for expression in said cells according to the invention.

BRIEF DESCRIPTION OF THE DRAWINGS

The detailed description which follows is designed to illustrate other features and advantages of the present invention.

FIG. 1 shows the 2261-bp HindIII-HpaI cassette containing the sequences coding for human myeloperoxidase, and HindIII-SnaBI cassette.

The coding sequence begins at the ATG specifying the N-terminal methionine (Met) and ends with the TGA stop codon (***).

The sequences in bold type represent the synthetic oligonucleotides added at the 5' end and at the 3' end of the hMPO cDNA.

Figure 2:
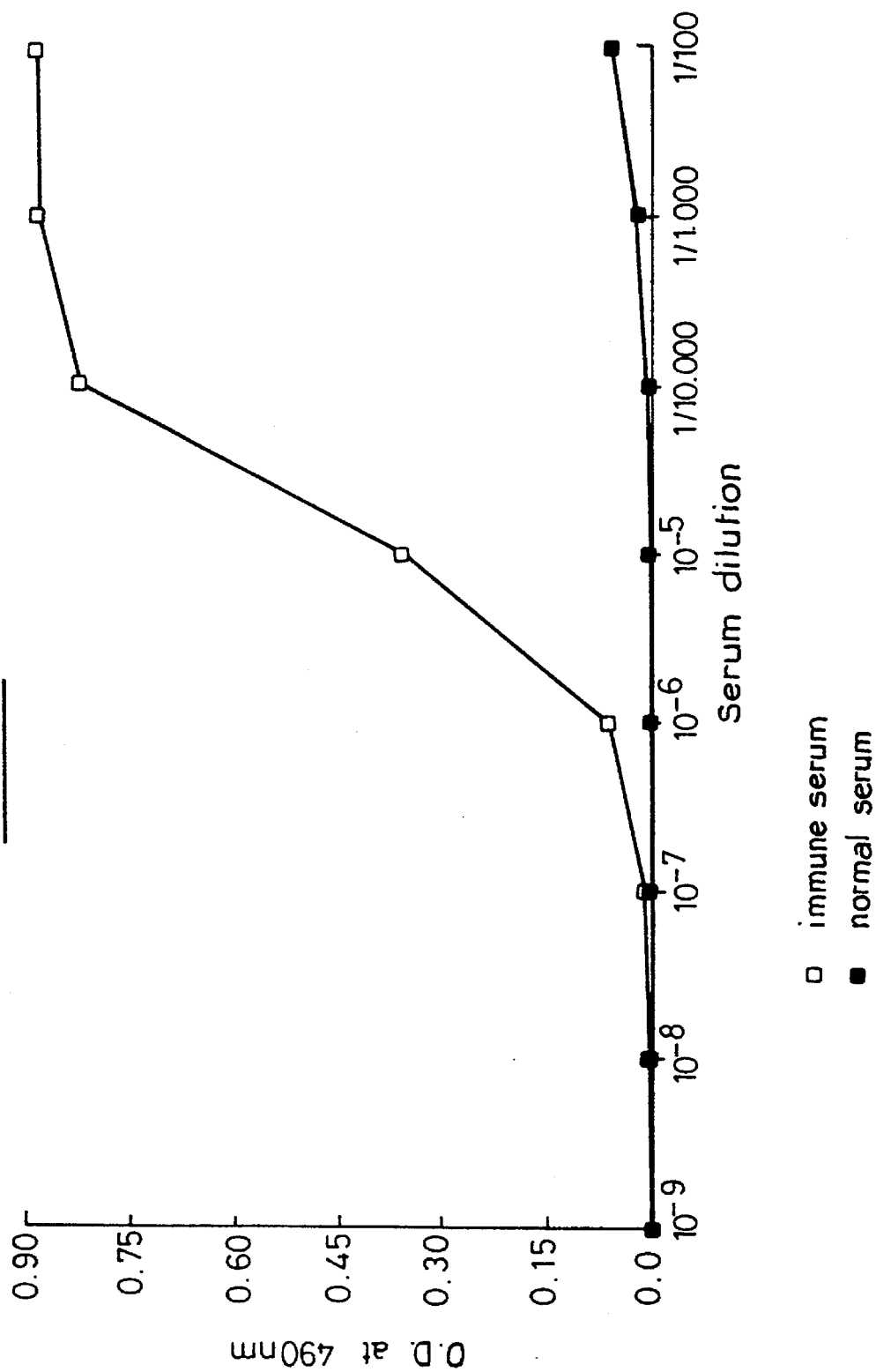

FIG. 2 shows the binding of rabbit sera into ELISA to MPO.

Figure 3:
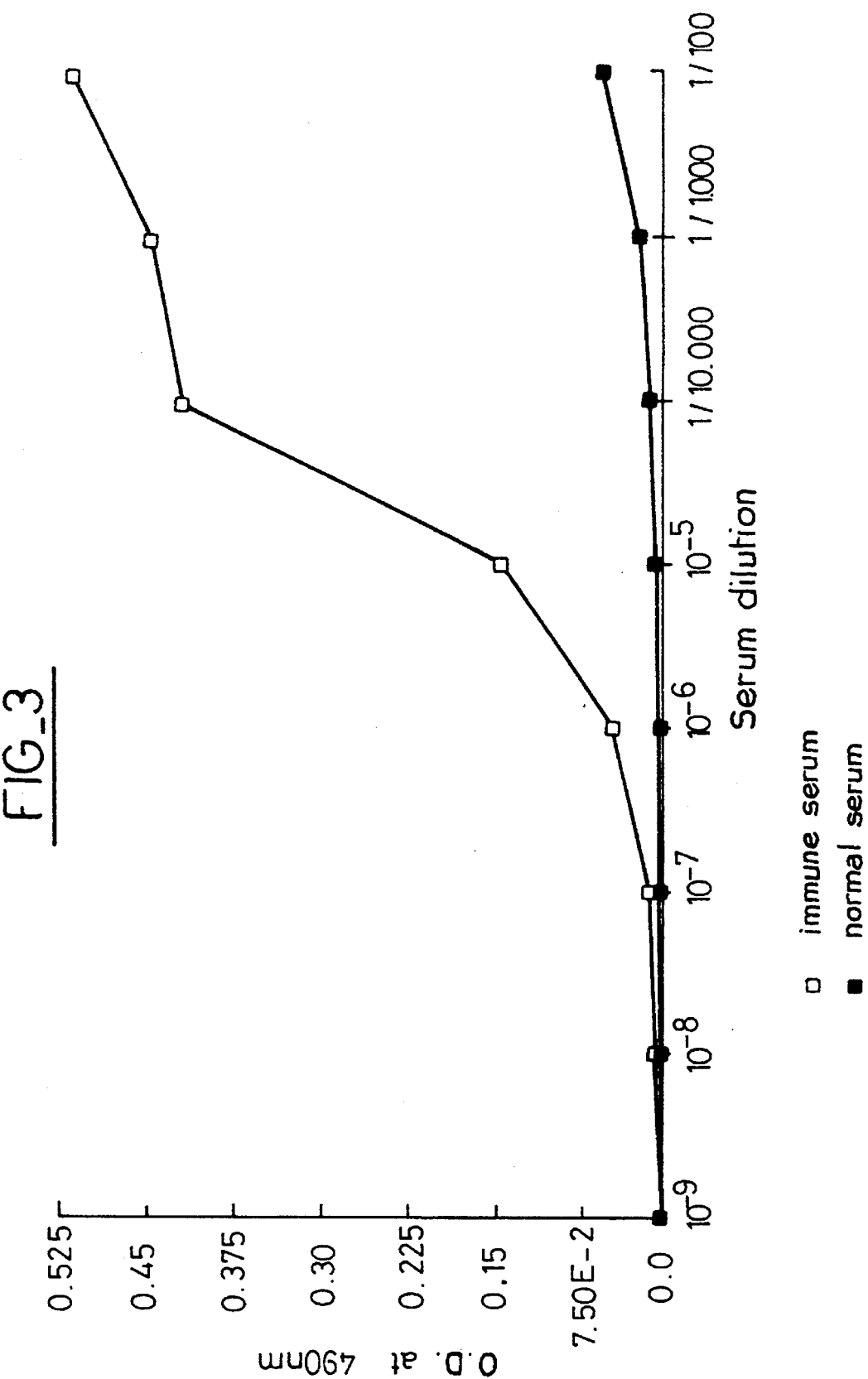

FIG. 3 shows the binding of mouse sera in ELISA to MPO.

Figure 4:
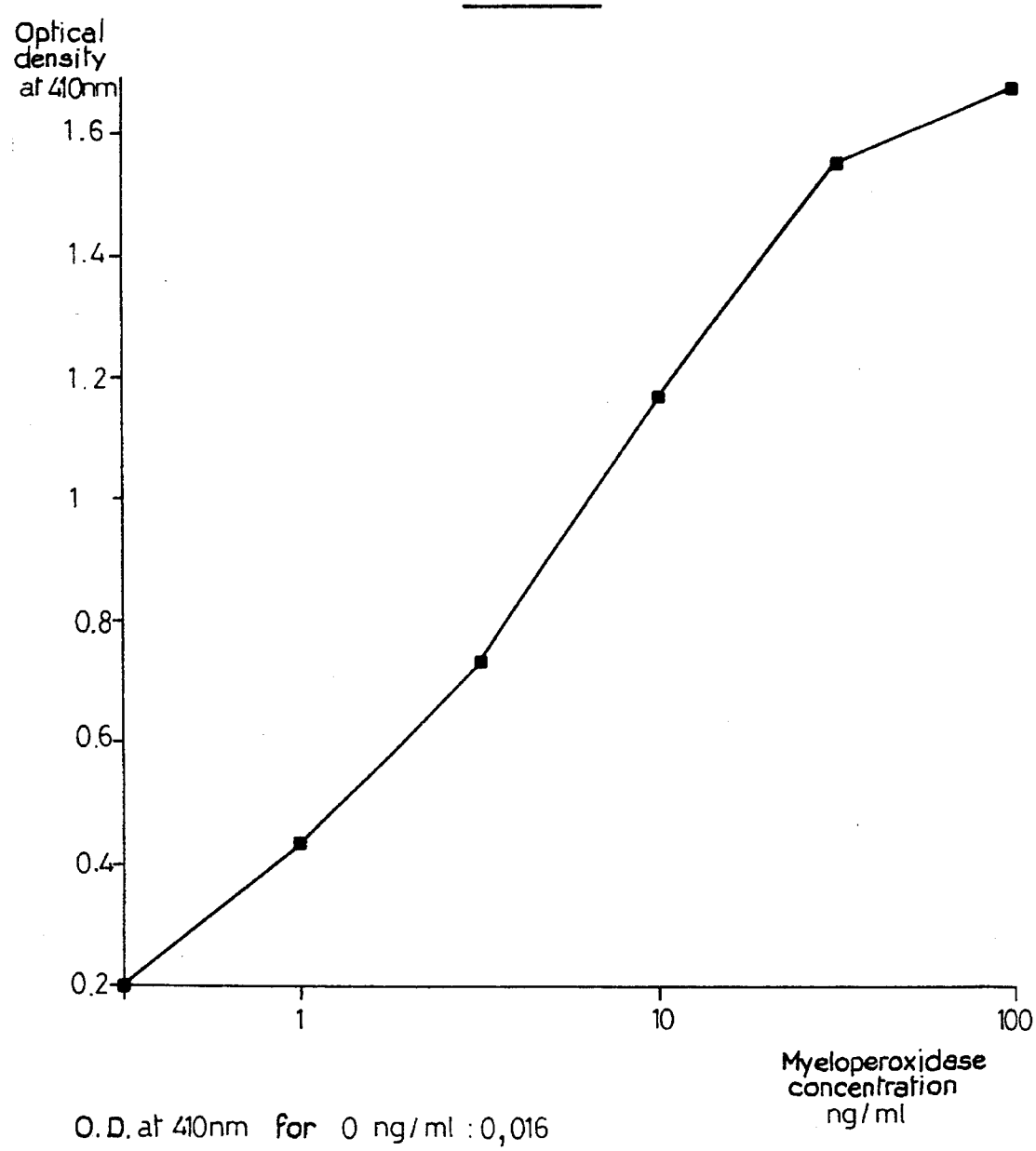

FIG. 4 shows a standard curve in an ELISA test for the detection of human myeloperoxidase.

Figure 5:
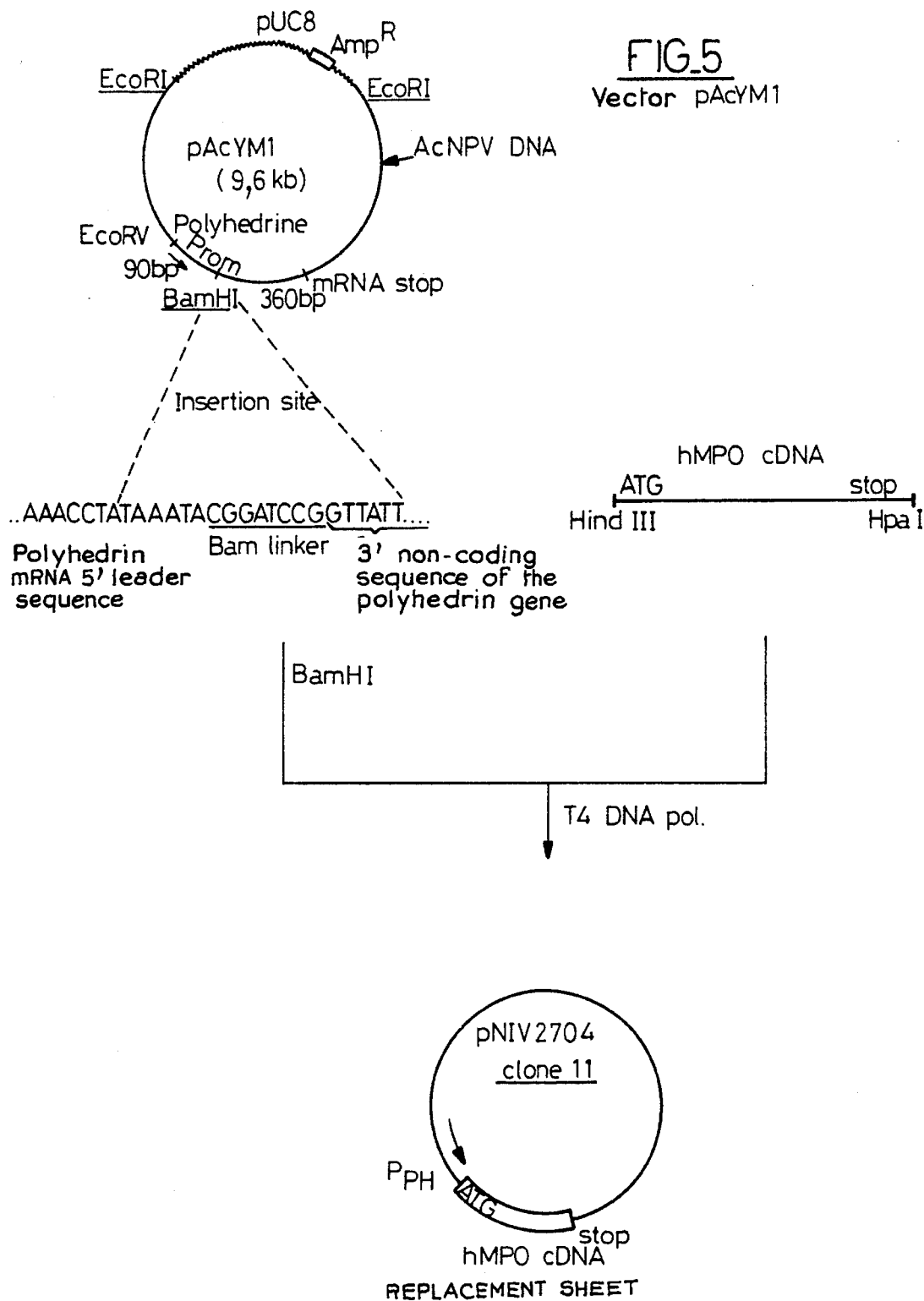

FIG. 5 shows the construction of the vector pAcYM1-MPO11 according to the invention (transfer plasmid for Baculovirus).

FIG. 6 shows the map of the Tnd vector from which plasmid pNIV2703 according to the invention is constructed.

The 3 cassettes direct, respectively, the expression of the DHFR and Neo™ selection markers, as well as that of a foreign cDNA (in the case illustrated above, it is that for t-PA). The latter cassette may be replaced by a cassette coding for any suitable cDNA, turning to good account the single restriction sites flanking the t-PA cassette.

Abbreviations

SV early: early promoter of SV40;

5: non-coding extensions at the 5' end;

3: non-coding extensions at the 3' end;

SV: polyadenylation region of SV40;

Rous LTR: (long) terminal repeat sequence derived from Rous sarcoma virus;

bGH: polyadenylation region of the bovine growth hormone gene;

Betablopro: main promoter of murine β-globulin.

FIG. 7 shows a map of pNIV2703, 2705 and 2706. The mammalian expression vector has been described before ((14) in example 2). The three cassettes direct the expression of a DHFR selectable marker, recMPO and a Neo™ selectable marker. Sequences encoding the recMPO modules are inserted between the HindIII and SnabI sites. Sequences derived from pUC19 are flanked by unique NotI flanking sites. pNIV2703 contains the recMPO cDNA starting at the first ATG (Met1), pNIV2705 and pNIV2706, the cDNA's starting at the second and third in frame ATG codons (Met12 and Met27 on the protein sequence, respectively). Details on the construction of the three distinct recMPO modules are given in the miniprint section.

Abbreviations

SV ORI: SV40 origin of replication;

Rous LTR: Rous sarcoma virus long terminal repeat promoter;

bGH: bovine growth hormone polyadenylation region;

PGLO: mouse major β-globin promoter.

FIG. 8 shows SDS-PAGE and Western blot of purified recMPO. RecMPO, eluted from the copper chelate sepharose column, was analyzed by SDS-PAGE. Proteins were detected by silver staining (panel A) or by immunoblotting (panel B). See legend to FIG. 6 for details.

Lanes 1 and 3: recMPO

Lanes 2 and 4: natural MPO (commercial preparations of MPO contains usually significant amount of an unprocessed precursor).

Molecular weight standards are indicated by arrows.

Figures 9, 10:
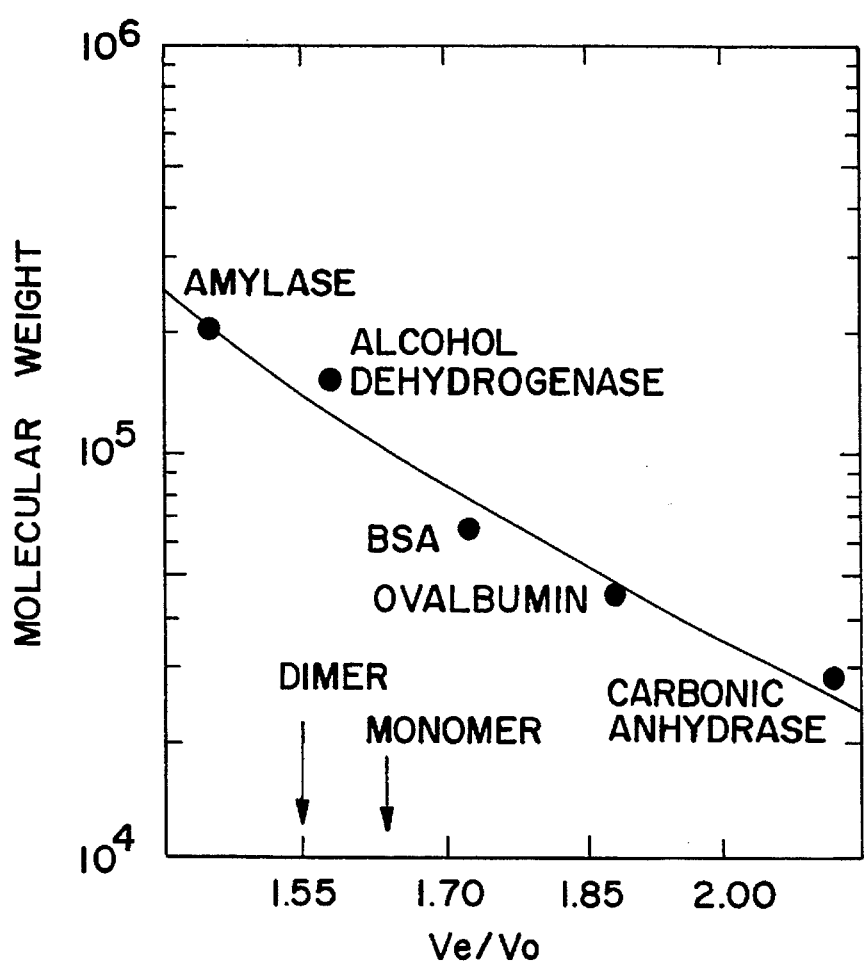

FIG. 9 shows amino-terminal amino acid sequence of the purified 84 kDa recMPO. The sequence spans residues 47 to 65 of the MPO amino acid sequence deduced from the cDNA. Underlined residues were identified as PTH amino acids by automated Edman degradation. Brackets show unidentified amino acids.

FIG. 10 shows separation of monomeric recMPO and dimeric natural MPO by gel filtration chromatography. Purified 84 kDa recMPO or natural MPO was loaded onto a Sephacryl S200 column (124× 1.5 cm which was eluted with 0.25M $KPO_4$ buffer, pH 7.5 at a flow rate of 10 ml/hour. Two ml fractions were analyzed for absorption at 280 nm and for activity to identify the MPO enzyme. A calibration curve was obtained by chromatographying standard proteins on the column using identical conditions. The elution positions of natural (DIMER) and recombinant MPO (MONOMER) are indicated by arrows. The void volume (Vo) was determined by using blue dextran.

FIGS. 11a–d show physico-chemical characterization of recMPO. Purified recMPO (10 µg/ml in sodium phosphate-citrate buffer 0.1M pH 5.0) was compared to the natural enzyme (10 µg/ml) in terms of enzymatic stability in various pH, temperature, ionic strength and reducing conditions. Residual activity of the enzyme (in %) was measured using the OPD-based activity assays (see Material and Methods).

A, activity versus pH; B, activity versus temperature; C, activity versus ionic strength (NaCl); and D, activity versus reducing agents (Dithiothreitol)

A, activity versus pH o-o-o-/●-●-●- natural/recMPO activity versus temperature

-□-□-□/-■-■-■ natural/recMPO at 60° C.

-o-o-o/-●-●-● natural/recMPO at 15° C.

-Δ-Δ-Δ/-▲-▲-▲ natural/recMPO at 82° C.

C, activity versus ionic strength (concentration of NaCl) natural/recMPO

-o-o-o/-●-●-● natural/recMPO

Figure 12:
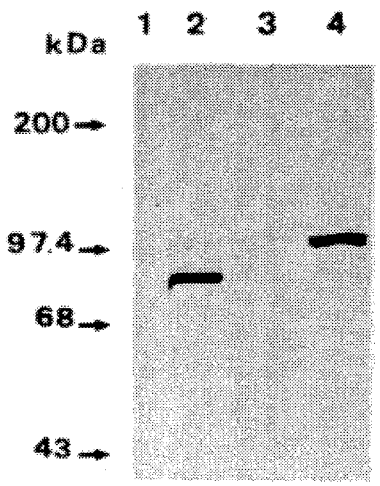

D, activity versus reducing agents (DTT) natural/recMPO
-o-o-o/-●-●-● natural/recMPO FIG. 12 shows immunodetection of recMPO in the CHO cell line 24.1.7 cultivated for 24 h in the presence of tunicamycin. Cell extracts and spent culture medium were analyzed on 7.5% SDS-polyacrylamide gel. Proteins were then blotted onto nitrocellulose sheets and reacted with rabbit antihuman MPO serum followed by treatment with an alkaline phosphatase-labelled protein A and the chromogenic substrate. Molecular weights, in kDa, are indicated on the left side of the figure. Lanes 1 and 2, spent culture medium and cell extract of clone 24.1.7 cultivated in the presence of tunicamycin; lanes 3 and 4, spent culture medium and cell extract of clone 24.1.7, cultivated without tunicamycin.

Figure 13:
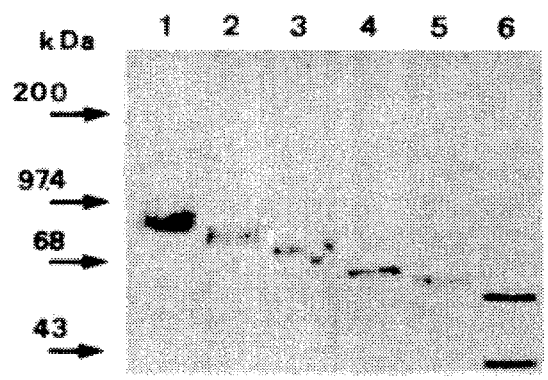

FIG. 13 shows immunodetection of recMPO digested with N-glycosidase F or endoglycosidase H. Purified natural or recombinant MPOs were digested with either N-glycosidase F or endoH. Samples were analyzed as described in the legend of FIG. 12. Molecular weight standards are indicated by arrows.

Lane 1, recMPO, untreated; lane 2, recMPO digested with endoH; lane 3, recMPO treated with N-glycosidase F; lane 4, natural MPO; lane 5, natural MPO treated with endoH and lane 6, natural MPO digested with N-glycosidase F.

Note: Heat denaturation of natural MPO before sample digestion generates a truncated fragment of 41 kDa ((31) in example 2).

Figure 14:
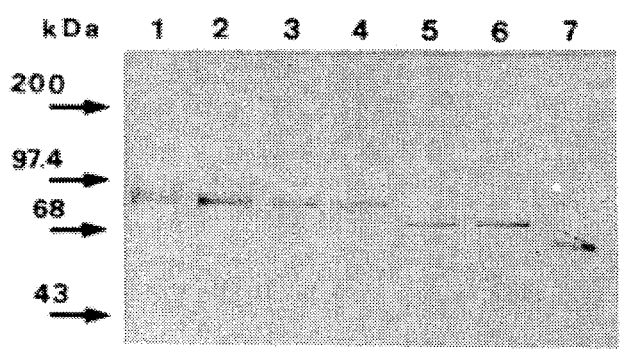

FIG. 14 shows sequential digestion of recMPO with glycosidases. Purified recMPO was sequentially digested with various glycosidases. Samples were analyzed as described in the legend of FIG. 12. Molecular weight standards are indicated by arrows. Lane 1, untreated recMPO; lane 2, digestion with sialidase; lane 3, further digestion with β-galactosidase; lane 4, additional digestion with β-N-acetylglucosaminidase; lane 5, recMPO digested with N-glycosidase F; lane 6, fully deglycosylated recMPO (digested with neuraminidase, O-glycosidase, N-glycosidase F, and lane 7, natural MPO (heavy chain).

FIG. 15a–f represent the deduced amino acid sequence of the 84 KDa recombinant MPO, the amino acid sequence of the secreted 84 KDa recombinant MPO residues 49 to 63 having further been identified by Edman degradation.

DETAILED DESCRIPTION OF THE PREFERRED EMBODIMENTS

Example 1

Preparation of hMPO by Genetic Engineering

A. Construction of a Cassette Containing the Totality of the Sequences Coding for Human Myeloperoxidase Flanked by Restriction Sites Absent from the cDNA for Myeloperoxidase (MPO)

1. Object

Production of a HindIII/HpaI cassette containing the sequences coding for human MPO and which can be inserted in different expression vectors.

2. Starting Material bacterial plasmid pMPO62 containing a complete cDNA for human MPO (Johnson et al. 1987, Nucleic Acids Research 15, 2013–2026);

any cloning vector containing appropriate restriction sites. Our choice fell on plasmid pTNDPC2, a plasmid derived from pTND (Connors et al., 1988, DNA 7, 651–661). Plasmid pTNDPC2 is not essential for obtaining said cassette; it would have been entirely possible to use another cloning vector containing the necessary restriction sites, such as plasmid pJRD184 (Heustersreute et al., Gene 39 (1985) 299–309).

3. Production of Oligonucleotides by Chemical Synthesis

To obtain a HindIII site directly upstream from the 10 hMPO ATG, we chose to synthesize, by means of chemical methods well known in our field, a pair of oligonucleotides which, when rehybridized with one another, contain, in the 5'-3' direction of the coding strand, a HindIII restriction site, the bases ACC, the sequences coding for the first 11 amino acids and the 1st base of the triplet of the twelfth amino acid of hMPO, which straddles an NsI1 site. These oligonucleotides are designated MPOIII and NPOIV (diagram 1 below).

To obtain an HpaI site downstream from the hMPO stop codon, a second pair of oligonucleotides was synthesized. When rehybridized, the latter have, in the 5'-3' direction on the coding strand, the last two bases of the triplet for amino acid 731, the sequence coding for the last 14 amino acids of hMPO, a stop codon (TGA) different from the natural stop codon of hMPO and fifteen bases containing an EcoRV site, an SnaBI site and the complement of an HpaI site. These oligonucleotides are designated MPOI and MPOII (diagram 1 below).

4. Subclonings

Subcloning 1

A 2053-bp (base pairs) NsI1-BglII fragment was extracted from plasmid pMPO62. This fragment and the 42-bp synthetic HindIII-Nsi1 fragment obtained by rehybridization of the oligonucleotides MPOIII and MPOIV were ligated to a 6755-bp HindIII-bglII fragment of pTNDPC2. The resulting plasmid pscMPO1 was introduced into *Escherichia coli* strain MM294, according to a well known method, with the object of producing plasmid pscMPO1 in larger amounts. Plasmid pscMPO1 thus contains a 2095-bp fragment extending from a HindIII site to a BglII site located approximately at amino acid 696 of hMPO.

Subcloning 2

A 1825-bp Xba1-Pst1 fragment was extracted from plasmid pMPO62. This fragment and the 62-bp synthetic Pst1-Hpa1 fragment obtained by rehybridization of the oligonucleotides MPOI and MPOII were ligated to a 3283-bp Xba1-Hpa1 fragment of TNDPC2. The resulting plasmid pscMPO2 was introduced into *Escherichia coli* strain MM294 with the object of producing it in larger amounts.

Plasmid pscMPO2 hence contains a 1887-bp fragment extending from an Xba1 site beginning with the first base for amino acid 123 of hMPO to an Hpa1 site.

5. Construction of Plasmid pNIV2702 from pscMPO1 and pscMPO2

In order, finally, to obtain the HindIII-HPa1 hMPO cassette, a 374-bp HindIII-Xpa1 fragment containing the sequence coding for amino acids 1 to 122 of hMPO and a 1887-bp Xba1-Hpa1 fragment containing the sequence coding for amino acids 123 to 745 of hMPO were extracted respectively, from plasmid pscMPO1 and pscMPO2. These two fragments were then religated to a 5165-bp HindIII-Hpa1 fragment of TNDPC2 to obtain plasmid pNIV2702.

Plasmid pNIV2702 hence contains a 2261-bp HindIII-Hpa1 cassette carrying the totality of the sequences coding for hMPO (FIG. 1). This cassette can be readily extracted and transferred into different expression vectors for hamster ovary cells (CHO) or for insect cells (*Spodoptera frugiperda*) via the baculovirus.

several control enzyme restrictions on 48 clones, clone 11 was identified as having the MPO insert in the correct

MPOI

```
                                                              stop
        GT ACACTT CCT GCATT GAACCT GGCTT CCT GGAGGGA AGCCT CCT GAT ATCT ACGT AT GGTT 3'
3' ACGT CAT GT GAAGGACGT AACT T GGACC GAAGGACCT CCCT T CGGAGGACT AT AGAT GCAT ACCAA 5'
```

MPOII
    PstI

| | | EcoRV | SnaBI | HpaI |
|---|---|---|---|---|
| | MPO 3' terminus | | | |
| Met | | MPOIII | | |
| 5' AGCTT ACC ATGGGGGTT CCCTT CTT CT CTT CT CT CAGAT GCA | | 3' | 42-mer | |
| 3'    AT GGT ACCCCC AAGGGAA GAA GAGAA GAGAGT CT | | 5' | 34-mer | |
| | | MPOIV | | |
| HindIII | | NsiI | | |
| | MPO 5' terminus | | | |

Diagram 1

B. Development of an ELISA Test for the Detection of Natural and Recombinant Myeloperoxidase a. Production of Anti-MPO Antibodies Anti-MPO sera were obtained in rabbits and mice. They were tested in ELISA on MPO. (The plate is coated with MPO and saturated with BSA. The test antibodies are added, followed by an alkaline phosphatase/anti-Ig conjugate). In both cases, a titer of anti-MPO antibodies at least 8,000-fold higher in the immune serum than in a normal serum is obtained (FIGS. 2 and 3).

b. Development of the Test

A "sandwich" test was carried out using rabbit anti-MPO Ig (Prosan-Dakopatts A398) and one of our mouse anti-MPO sera. The plate is coated with rabbit Ig at a concentration of 7.6 gamma/ml in PBS pH 7.8, overnight at 4° C. It is saturated with 1% BSA in PBS pH 7.8/0.05% Tween 20 for 1 h 40 min at room temperature. The test samples are left for 2 hours at room temperature, followed by the mouse serum, diluted 1,000-fold in the saturation solution, for 2 h at room temperature, and finally alkaline phosphatase/rabbit antimouse Ig Fab2 conjugate (Prosan-Dakopatts D314) diluted 1,000-fold in TBS buffer (0.05M Tris-HCl pH 7.5, 0.15M NaCl) containing 1% BSA and 0.05% Tween 20. Between each step, the plate is washed 5 times with either TBS/0.05% Tween 20 (before and after application of the conjugate) or PBS/Tween 20 (other steps). Visualization is carried out by means of a solution of para-nitrophenyl phosphate at a concentration of 1 mg/ml in 10% diethanolamine, 0.01% $MgCl_2.6H_2O$, 0.02% $NaN_3$ pH 9.8, and the reaction is stopped with 3M NaOH. Reading is carried out at 410 nm. FIG. 4 shows a binding curve for a pure MPO (Green Cross Corporation) diluted in an SFMJ insect cell culture supernatant (TC100 medium with 10% FCS). It is seen that the test is useful for assaying MPO in a concentration range of between 0.1 ng/ml and 100 ng/ml.

C. Cloning of MPO cDNA into the Transfer Plasmid for Baculovirus

The DNA of the transfer plasmid pAcYM1 (Baculovirus (ref.: Matsuura et al. J. Gen. Virol (1987) 68, 1233–1250 was linearized with BamHI and mixed with the 2261-bp HpaI-HindIII DNA fragment corresponding to MPO. The mixture was treated with T4 DNA polymerase, ligated and used for transforming competent *E. coli* MM294 cells. Selection of the clones was carried out by growth on ampicillin. After orientation relative to the polyhedrin promoter (pNIV2704) (FIG. 5).

The synthetic oligonucleotides/MPO junctions added at the 5' end and at the 3' end to the MPO cDNA during the above constructions were confirmed by sequencing these regions. The sequencing method on double stranded DNA/a with sequenase was used.

Cotransfection and Plaque Assay

The recombinant plasmid 11 was used in conjunction with the wild-type viral DNA for cotransfecting *Spodoptera frugiperda* cells (Sf9) in culture (the protocol is well known and is detailed in the manual by M. D. Summers and G. E. Smith, "A Manual of Methods for Baculovirus Vectors and Insect Cell Culture Procedures," Texas University, College Station, 1987).

The cotransfection supernatants of days 5 and 7, after homologous recombination, were used in a plaque assay as to have 100 to 1,000 lyric plaques per dish. The recombinant viruses not containing polyhedrin were identified 5 days later, visually or by DNA hybridization. 13 candidates were subcultured and purified.

Test of Production of Recombinant MPO

Two recombinant Baculoviruses, designated MPO1.1 and MPO5.2, were used for infecting Sf9 cells and measuring the capacity of the latter to produce myeloperoxidase. In both cases, the infected cells secrete into the culture medium a protein recognized specifically by anti-myeloperoxidase antibodies, and the quantity of which was evaluated by an ELISA test at $\simeq 0.2$ μg/ml. (The infected cells were harvested at a density of $10^6$ cells/ml). The recombinant product was also to be found in the crude cell extract in the proportion of $\simeq 0.06$ μg/$10^6$ cells.

Cotransfection of Sf9 (*Spodoptera frugiperda*) Insect Cells

Use of the recombinant vector (pNIV2704) pAcYM1/ MPO 11 constructed, containing MPO downstream from the baculovirus promoter of polyhedrin, 100 μg used in conjunction with 1 μg of viral DNA.

Calcium Chloride Transfection Technique

Use of the 5-d cotransfection supernatant for the plaque assay. Dilutions of −1 to −7, dishes per dilution.

Use of the 7-d supernatant under the same conditions.

The harvested supernatants were used for producing lyric plaques in Sf9 cell monolayers (cell infection—3 million per dish— with dilutions of the cotransfection supernatant, for 60'. Remove the inoculum and cast a layer of low melting point agar, 1.5% final. Cover with J. R. Scientific EX-Cell 400 medium with added antibiotics and leave in the incubator at 28° C. for 4 days). Staining of the dishes with neutral red after 4 d of infection and hybridization of filters with an [$\alpha^{32}$P]-dCTP-labeled MPO DNA fragment.

Subculturing of 13 Candidates on the Basis of Autoradiography

Two plaque assay purifications were then carried out successively.

D. Cloning of hMPO cDNA into the pTDN Expression Vector for Mammalian Cells (CHO) and Introduction into the Cells 1. Protocol a. Production of the Expression Vector pNIV2703:

With the object of eliciting hMPO production by Chinese hamster ovary (CHO) cells, we introduced the 2253-bp HindIII-SnaBI cassette of pNIY2702 carrying the sequences coding for hMPO between the HindIII and SnaBI sites of the mammalian expression vector pTDN. The pTDN vector, the principle of use of which is identical to the pTND vector (Connors et al., 1988) from which it is derived, carries 2 genes encoding selection markers [resistance to neomycin (bacterial neophosphotransferase, Neo™) and dihydrofolate reductase (DHFR)] and a cassette for expression of the molecule of interest, in this case ht-PA (human tissue plasminogen activator). The manipulation described above hence consists in replacing the HindIII-SnaBI cassette carrying the totality of the sequences coding for ht-PA by that encoding hMPO. When this replacement had been accomplished, the recombinant plasmid obtained, pNIV2703, was introduced into E. coli strain MM294 with the object of purifying it in a sufficient amount for the transfection of CHO cells. FIG. 6 depicts diagrammatically the pTND expression vector (Connors et al., 1988). The pTDN vector corresponds to the pTND vector apart from the fact that the DHFR cassette has a reverse reading order and is localized between the neo cassette and the t-PA cassette.

b. Transfection by Electroporation of CHO Cells

By means of a digestion with the restriction enzyme Not1, the sequences of bacterial origin (PUC19 in FIG. 6 were separated from the fragment carrying the 3 expression cassettes for mammalian cells. When digested, the vector pNIV2703 is introduced by electroporation, a method of transfection in CHO DHFR⁻ cells according to a method similar to that described by Zerbib et al. (1985, Biochem. Biophys. Res. Comm. 129, 611–618). The cells were then placed in a growth medium containing G418, which does not permit the survival of cells not expressing the neophosphotransferase. Thus, after a period of 1 to 3 weeks, only the cells which have acquired the appropriate selection gene carried by the vector pNIV2703 survive and multiply. The cell clones thereby obtained were finally tested for the expression of hMPO. To this end, the culture supernatant and a cell extract of each of these clones was analyzed by means of an ELISA (Enzyme Linked Immunosorbent Assay) test enabling the hMPO to be qualified and quantified specifically.

The results show that the recombinant clones secrete recombinant MPO into the culture medium. The level of production, estimated by ELISA, is between 0.1 and 1 mg per ml of supernatant.

Example 2

Secretion of Enzymatically Active Human Recombinant Myeloperoxidase by Chinese Hamster Ovary Cells in Culture Summary The cDNA encoding human myeloperoxidase carries three ATG codons in frame, respectively 144, 111 and 66 bp upstream from the proprotein DNA sequence. In order to determine the most efficient signal sequence, three cDNA modules starting at each of the ATG were cloned into an eukaryotic expression vector and stably expressed in Chinese Hamster Ovary cell lines. In all three cases, recombinant MPO was secreted into the culture medium of transfected cells, indicating that each of the signal peptides functions efficiently. One of the recombinant cell lines, which was amplified using methotrexate, overexpresses enzymatically active recMPO up to 6 μg/ml/day. The recombinant product was purified by a combination of ion exchange and metal chelate chromatography and characterized in terms of molecular weight, N-terminal amino acid analysis, glycosylation, activity and physico-chemical properties. The data show that recMPO is secreted essentially as a heme-containing single chain precursor of 84 kDa which functions as a monomer. N-terminal analysis indicated that cleavage of the signal peptide occurs between amino acids 48 and 49. In addition, recMPO appeared glycosylated up to the last stage of sialylation, to an extent similar to the one of the natural enzyme. At last, specific activity measurements as well as stability data, in various pH, T°, ionic strength and reducing conditions, indicated that the recombinant single chain enzyme behaves essentially as the natural two chains molecule.

Introduction

Myeloperoxidase (EC 1.11.1.7) is a heme-containing glycoprotein localized in azurophilic granules of polymorphonuclear leukocytes (1). The enzyme plays a major role in the host defense function of these phagocytic cells by generating strongly oxidant molecules (2), and modulates various substances generated in response to inflammation (3). Myeloperoxidase (MPO) has been purified from leukocytes and myeloid leukemia HL-60 cells (4–7). It appears as a dimer composed of two light chains of 15 kDa and two heavy chains of 59 kDa. In addition to this large molecular weight dimeric enzyme, HL-60 cells secrete a single chain, monomeric and unprocessed polypeptide of 89 kDa which displays enzymatic activity (8).

The cDNA coding for MPO has been cloned and characterized (9–11); the sequence codes for a protein of 745 amino acids specifying the preform of the molecule. The 5' coding region carries three ATG codons in frame, corresponding respectively to positions 1, 12 and 27 on the preproprotein sequence. It is assumed that the first ATG triplet functions as the initiation codon but no data are available regarding the actual size of the signal peptide for the protein. Recent information, however, suggests that cleavage of the prepeptide occurs between amino acids 48 and 49 of the 745 amino acid sequence deduced from the MPO cDNA (12). In any case, the processing of MPO appears rather complex since the preform is sequentially processed into shorter intermediates to yield a mature two chain enzyme which is eventually stored as a dimer in azurophilic granules (13).

In order to define more precisely the relationship between structure and activity of MPO, we have stably expressed the corresponding cDNA in a CHO cell line. The data indicate that recMPO is efficiently secreted into the cell culture medium, whatever the length of the signal peptide, which originates either at Met1, Met12 or Met27.

Biochemical analysis of purified recMPO, isolated from the amplified cell line 24.1.7, demonstrated that the product is synthesized as a monomeric single chain, unprocessed but enzymatically active glycoprotein. In addition, N-terminal amino acid analysis showed that the secreted recombinant product starts at residue 49 in the protein. At last, on the basis of several physico-chemical criteria, there is strong evidence that recMPO is functionally undistinguishable from the natural enzyme.

Results

Construction of recMPO Coding Sequences

The cDNA coding for MPO, carried by plasmid pMP062 (10), contains three closely linked ATG codons in frame in the 5' terminal part of the molecule. Because the first ATG is usually the initiation codon of eukaryotic mRNA's (24), it has been tentatively assigned as the initiation signal for human preproMPO (9). If this is really the case, the derived signal sequence of MPO would be unusually long since the signal petidase appears to cleave between residues 48 and 49 of the protein (12). In order to find out if any of the other two ATG codons function as initiation codons, and subsequently, if the resulting shortened signal sequences are still efficient for secretion, we constructed three distinct coding modules starting at each of the three ATGs and inserted them into the eukaryotic expression vector pTND (14). The resulting recombinant plasmids, pNIV2703, 2705 and 2706, thus differ by the length of the sequence separating the ATG from the cleavage site of the signal sequence (FIG. 7). The distances are respectively 144, 111 and 66 bp which correspond to signal peptides of 48, 37 and 22 amino acid residues.

Expression of recMPO in Cell Cultures

CHO dhfr⁻ cells were transfected with the recombinant plasmids described above and selected for resistance to G418. Colonies appeared after 1 to 2 weeks following transfection. Assay of the recombinant polypeptides by ELISA indicated that most of the clones secreted MPO-like material at levels ranging between 100 and 2500 ng/ml/24 hours approximately. In addition, it was found that the nature of the recombinant plasmid used for transfection, pNIV2703, 2705 or 2706, has no incidence on the secretion capability of the cells on the average level of MPO production either. In view of these results, any of the recombinant G418 resistant cell line could thus be picked up for amplification. Several G418 resistant clones, deriving from the transfection with plasmid pNIV2703, were exposed to increasing concentrations of MTX to coamplify the DHFR and the MPO sequences. Initial selection started at 5 nM MTX and yielded cell lines secreting higher levels of MPO; a second selection at 100 nM MTX gave rise to cells with production levels raised up to 1968 ng/ml/24 hours (Table II). Another independent amplification of three other G418 resistant clones up to 25 nM MTX led to greater production: from 958 to 2657 ng/ml/24 hours (Table II). Selection with higher MTX concentration although giving rise to resistant colonies did not increase production further.

Purification of Enzymatically Active recMPO

Recombinant MPO was purified to homogeneity starting from 3-days cultures of the cell line 24.1.7 in production medium (1% FCS). Table III summarizes the results of the purification procedure. Nearby 90% of the recMPO activity was recovered after the Q-Sepharose column and nearly two thirds of the contaminating proteins were eliminated. After chromatography onto the CM-Sepharose column, recMPO was purified 66 fold with a yield of 82%. The last step, which consisted of a copper chelate sepharose column, produce essentially pure recMPO by removing residual contaminants. The final product had a specific activity of 537 Units/mg, measured with orthophenylenediamine as substrate, and was recovered with an overall yield of 72.3%. Purified recMPO, when analyzed on SDS-PAGE, migrated as a major 84 kDa species and a minor 94 kDa molecule (FIG. 2). Spectophotometric analysis of the recMPO showed two distinct absorption maxima at 430 and 280 nm in a ratio of 0.6, indicating the presence of a hemic structure in the recombinant enzyme. The purified recMPO was assayed for enzymatic activity in vitro using O-dianisidine and was found to display a specific activity of 0.8 U/µg, which is similar to the one of natural MPO.

Characterization of recMPO

The purified 84 kDa recMPO was submitted to N-terminal amino acid analysis. The sequence was found to begin with Ala49, indicating that cleavage of the signal peptide occurred between Gly48 and Ala49 as reported previously (12). The results of the sequence analysis are shown in FIG. 9.

In order to determine whether recMPO is secreted as a monomer, like the precursor produced by HL-60 cells (8), or as a dimer like the natural enzyme (5), the purified recombinant protein was compared to natural MPO by chromatography on a calibrated Sephacryl S200 column. The data show that recMPO elutes as a 90 kDa species whereas, as expected, natural MPO behaves as a 150 kDa dimer (FIG. 10). RecMPO, thus, is secreted by transfected CHO cells under an enzymatically active monomeric form.

RecMPO was further characterized in terms of physico-chemical properties; the stability of the recombinant enzyme was compared to that of the natural enzyme in various T°, pH, ionic strength and reducing conditions. As seen in FIG. 11, both enzymes behave identically for most of the tested parameters, except that recMPO appeared more sensitive to higher temperatures (>60° C.) than natural MPO. For both enzymes, however, maximal activity was observed around pH 5.0 in the presence of 200 mM NaCl, in agreement with data from the literature (25).

Carbohydrate Analysis of recMPO

To analyze the oligosaccharide structure of recMPO, three approaches were followed: in vivo inhibition of N-glycosylation with tunicamycin (26), sequential digestion in vitro of the purified recombinant enzyme with glycosidases and affinoblotting, which consists of reacting exposed sugar residues on the digested protein with sugar-specific lectins after gel electrophoresis and transfer on a nitrocellulose sheet.

A first experiment consisted of cultivating the cell line 24.1.7 for up to 72 hours in the presence of 5 µg/ml tunicamycin. Cells and spent culture medium were then analyzed on Western blots; as seen in FIG. 12, treatment with tunicamycin prevented the secretion of recMPO in the culture medium and led to the intracellular accumulation of a 77 kDa polypeptide. Its apparent molecular mass is consistent with that one of N-linked unglycosylated myeloperoxidase (27).

The subsequent assays were done on purified recombinant and natural MPO. Several glycosidases were used: N-glycosidase F, endoglysidase H (endoH), sialidase, β-galactosidase, β-N-acetylglucosaminidase and endo-α-N-acetyl-galactosaminidase (O-glycosidase). These enzymes function as follows: N-glycosidase F removes high mannose and complex N-linked oligosaccharide residues (28) and endoH cleaves high mannose and some hybrid structures (29), leaving a single N-acetyl glucosamine (GlcNac) attached to the protein. Sialidase removes sialic acid residues and β-galactosidase cleaves off exposed galactose groups. Successive digestions of asialo-proteins with β-galactosidase and β-N-acetylglucosaminidase remove all exposed galactose and GlcNac from N-linked oligosaccharides, leaving trimannosyl cores on the protein. O-glycosidase, at last, digest O-linked oligosaccharides from asialoproteins (30).

Actual experiments started with the treatment of MPO enzymes with N-glycosidase F and endoH. Samples, previously denatured with 1% SDS, were digested then analyzed by SDS-PAGE and Western blotting. As seen in FIG. 13 recMPO treated with N-glycosidase F shifted in size from 84 to 71 kDa (lane 3). Similarly, the heavy chain of natural MPO migrated at 52.5 kDa instead of 61.5 kDa (lane 6; there was no change in the apparent mass of the light chain of the natural enzyme, data not shown). From the shifts in apparent molecular masses, both recombinant and natural MPO's appear N-glycosylated to a roughly similar extent (15% versus 12% respectively). With respect to endoH susceptibility, both recombinant and natural MPOs displayed mobility changes on polyacrylamide gels. As seen in FIG. 13 (lanes 2 and 5), recMPO lost about 6.5 kDa and the heavy chain of natural MPO, about 3.5 kDa. These shifts in apparent molecular masses indicate that recMPO has a high mannose content of 7.7%, clearly superior to the level found in the natural enzyme (4.6%).

Further experiments aimed at the obtention of fully deglycosylated recMPO; to this end, sequential digestion of recMPO was achieved with sialidase, β-galactosidase, β-N-acetylglucosaminidase, N-glycosidase F and O-glycosidase. As seen in FIG. 14, products resulting from these digestions had apparent molecular masses of 81.7, 80.6, 80.6, 71.3 and 71.3 kDa respectively.

In order to verify the completion of the digestions with the various glycosidases and to determine the precise carbohydrate structure of recMPO, digested samples were transferred onto nitrocellulose sheets and exposed to various sugar-specific lectins conjugated to alkaline phosphatase.

Seven lectins were used; they are SNA, MAA, RCA, PHAE, PNA, WGA and GNA (their specificities are detailed in the legend of Table IV).

As seen in Table IV, intact recMPO and natural MPO react with the MAA, RCA, WGA and GNA lectins. This shows that both enzymes carry terminal sialic acid linked in $\alpha(2-3)$ to galactose residues, have terminal galactoses linked in $\beta(1-4)$ to N-acetylglucosamine, contain N-acetylglucosamine as dimers and display terminal mannose residues, either as high mannose N-glycan chains or as exposed mannose in hybrid chains. Moreover, the reactivity with PHAE indicates that recombinant and natural MPO have the trisaccharide Gal $\beta(1-4)$, GlcNac $\beta(1-2)$ Man linked in $\alpha(1-6)$ to mannose. These structures are confirmed by the concommitant disparition of specific lectin binding with the extent of deglycosylation. The absence of reactivity with the SNA lectin on intact MPO's indicates that these molecules do not have sialic acid residues linked to galactose in the $\alpha(2-6)$ position. In addition, the positive reaction of the PNA lectin with asialo-MPO's shows that the proteins are O-glycosylated, although to a small extent only since apparent molecular masses of O-glycosidase-treated MPO's do not differ significantly from those of N-glycosidase F-treated molecules (FIG. 14, lanes 5 and 6).

Discussion

In previous studies, human MPO has usually been purified from leukocytes of pooled peripheral blood samples (4.34). Significant heterogeneity has been observed in the product obtained along this route. More recently, promyelocytic leukemia HL-60 cells were used as starting material, allowing the characterization of intracellular and secreted single chain precursors of MPO in addition to the mature extracellular two chain enzyme (8,13).

In the present work, recombinant human MPO was produced in transfected and amplified CHO cells. The recombinant molecule was efficiently secreted into the culture medium in high yield and its purification was achieved in three straightforward steps. The pure product consisted of two single chain polypeptides, a major 84 kDa protein and a minor 94 kDa species.

It should be pointed out here that the length of the signal peptide does not appear critical for efficient secretion of active recMPO. Indeed, CHO cell lines transfected with any of the three distinct cDNA expression modules, pNIV2703, 2705 or 2706, were equally able to secrete active molecules. In each case, the length of the signal peptide was defined by the coding sequence separating the first, second or third in frame ATG codons, on the preproprotein sequence, from the signal peptide cleavage site.

N-terminal sequence analysis of the major 84 kDa recMPO indicated that it started at amino acid Ala49 in the preproprotein sequence and corresponds to the 89 kDa product described by Yamada et al. (12). We did not identify any immunoreactive material equivalent to the 84 kDa product, reported by these authors, which starts at amino acid residue 155 in the MPO sequence (12). It seems likely that the discrepancies in molecular mass observed between the 84 kDa recMPO and the 89 kDa precursor secreted by HL-60 cells result from experimental differences.

As concerns the minor 94 kDa recMPO product, we believe it corresponds to the 91 kDa precursor form identified intracellularly and in spent culture medium of HL-60 cells (22, 27, 35–38). In fact, studies on the biosynthesis of MPO in these cells indicated that the protein is initially synthesized in the rough endoplasmic reticulum as a large precursor carrying on its oligosaccharide chains, mannose 6-phosphate residues, which may be required for segregation and transport through the cell membrane.

Treatment of recombinant CHO cells with tunicamycin blocked secretion of MPO and led to the intracellular accumulation of a 77 kDa protein. This product which lacks N-linked oligosaccharides corresponds apparently to the in vitro translation product described by Hasilik et al. (27). Extensive analysis of the 84 kDa recMPO, using several glycosidases, indicated that it has a slightly higher sugar content than natural MPO (15% versus 12% of the total mass). This excess may be accounted for by an increase in high mannose content (7.7% versus 4.6%) and thus suggests that recMPO is not processed as efficiently as the natural enzyme in terms of high mannose trimming. Nevertheless, our data show that the glycosylation process proceeded up to the last stage, that is the addition of sialic acid residues.

The 84 kDa recMPO is produced as a monomer and is secreted as the proprotein molecule. It contains the typical hemic structure in view of its spectroscopic characteristics and is enzymatically functional with a specific activity similar to that one of natural MPO. The ratio A430 A280 of 0.6 is lower compared to that of the natural enzyme (0.8). This could be explained by a higher content in phenylalanine and tyrosine residues in the unprocessed recMPO (8).

The similarity between recMPO and natural MPO was further confirmed by stability studies in various pH, temperature, ionic strength and reducing conditions. Again, both enzymes function in a parallel way, except conventional preparation of MPO from polymorphonuclear leukocytes requires large volumes of blood an the overall purification yields are relatively low. The CHO cell system presented here outperforms largely the conventional approach since 2.5 mg of pure recMPO can be obtained from 1 liter of culture medium without major difficulties.

The abbreviations used are:

MPO: myeloperoxidase;
recMPO: recombinant myeloperoxidase;
CHO: Chinese Ovary Cells;
MTX: methotrexate;
dhfr: dihydrofolate reductase;
ELISA: enzyme-linked immunosorbent assay;
bp: base pairs;
aa: amino acid(s);
FCS: fetal calf serum;
G418: geneticin;
PBS: phosphate-buffered saline;
BSA: bovine serum albumin; and
SDS-PAGE: sodium dodecyl sulfate polyacrylamide gel electrophoresis.

EXPERIMENTAL PROCEDURES

Materials

Restriction endonucleases and T4 DNA ligase were purchased from Boehringer-Mannheim Biochemicals. Human leukocyte myeloperoxidase from Green Cross Corporation (Japan). Neomycin (Geneticin, G418), cell culture medium (αMEM) and L-glutamine were from GIBCO, methotrexate from SIGMA and fetal calf serum from Seralab.

Q-Sepharose FF, CM-Sepharose FF, Chelating Sepharose FF and Sephacryl S200 were purchased from Pharmacia-LKB Biotechnology.

Rabbit anti-human MPO serum, mouse anti-human MPO monoclonal antibody and rabbit anti-mouse serum conjugated to alkaline phosphatase were from Prosan Dakopatts and Protein A conjugated to alkaline phosphatase from Sigma.

Paranitorphenyl phosphate, O-dianisidine and orthophenylenediamine were respectively from Sigma, Janssen (Beers, Belgium) and Prosan Dakopatts. Acrylamide and bis-acrylamide were purchased from BDH, England. The Lectin Link Kit and the Glycan Differentiation Kit were respectively from Genzyme and Boehringer-Mannheim.

Construction of Expression Plasmids

Plasmids pMPO62 (10) and pTDN (14) have been described earlier. Plasmid pTDN PC2, provided by Dr. Reff, is a derivative of pTDN which is used only as an intermediate vehicle in plasmid construction.

All recombinant cDNA's described in this paper have been introduced in pTDN as HindIII-SnabI cassettes (FIG. 1.). The procedures for DNA preparation and restriction analysis were as published (15). Oligodeoxynucleotides were synthesized on an Applied Biosystem Synthesizer model 380A via the solid phase phosphoramidite method as previously described (16). Ligation and bacterial transformation of *Escherichia coli* K12 strain MM294 (endA, thr⁻, hsr⁻, hsm⁻) were performed according to (15). The method of Sanger et al. (17) was used for DNA sequence analysis.

pNIV2703

This recombinant plasmid codes for prepromyeloperoxidase. It has been constructed as follows: a 2053 bp NsiI-BglII DNA fragment was derived from plasmid pMPO62 (10); it encompasses the MPO molecule coding for aa 11 in the putative signal sequence to aa 696. The fragment was ligated, together with a synthetic 42 bp HindIII-NsiI DNA adaptor coding for aa 1 to 11 (adaptor 1, Table I), to the intermediate plasmid vehicle pTND PC2 cut with HindIII and EglII. The resulting recombinant plasmid pSCMPO1 thus encodes MPO from Met1 to Gln696. In parallel, a second DNA fragment (1825 bp) encoding aa123 to 731 of MPO was excised from pMPO62 (10) by digestion with XbaI and PstI and ligated, together with a synthetic 62 bp PstI-HpaI DNA piece coding for aa732 to the stop codon of MPO (adaptor 2, Table I), to the intermediate plasmid vehicle pTNDPC2 cut with HindIII and HpaI. The resulting recombinant plasmid, pSCMPO2 thus encodes MPO from Leu123 to the stop codon. For the next construction step, a 374 bp HindIII-XbaI DNA fragment derived from pSCMPO1 (aa 1 to 122 of MPO) and a 1887 bp XbaI-HpaI fragment derived from pSCMPO2 (aa 123 to the stop codon) were ligated to the plasmid pTNDPC2 to yield plasmid pNIV2702. The final construction was done by excising a 2253 bp HindIII-SnabI cassette from pNIV2702 and introducing it into the eukaryotic expression vector pTDN (14) cut with HindIII and SnabI. The resulting plasmid, pNIV2703, thus encodes the 745 aa long preproMPO under the control of the LTR promoter (FIG. 1).

TABLE I

Sequences of the synthetic DNA adaptors

ADAPTOR 1

```
              1              5                    10
             Met Gly Val Pro Phe Phe Ser Ser Leu Arg Cys M(et)
5' AGCTT ACC ATG GGG GTT CCC TTC TTC TCT TCT CTC AGA TGC A    3'
3'       AT GGT AC  CCC CAA GGG AAG AAG AGA AGA GAG TCT       5'
     HindIII                                            NsiI
```

TABLE I-continued

Sequences of the synthetic DNA adaptors

ADAPTOR 2

```
                    735                   740                  745
   (S)er Thr Leu Pro Ala Leu Asn Leu Ala Ser Trp Arg Glu Ala Ser
5'      GTACA CTT CCT GCA TTG AAC CTG GCT TCC TGG AGG GAA GCC TCC 3'
3' ACGT CATGT GAA GGA CGT AAC TTG GAC CGA AGG ACC TCC CTT CGG AGG 5'
   PstI
```

```
          stop
(con't) 5' TGAT ATCT ACGT ATGGTT 3'
(con't) 3' ACT AT AGAT GC AT AC CAA 5'
           EcoRV    SnaBI    HpaI
```

ADAPTOR 3

```
              12          15             20              24
          Met Lys Leu Leu Leu Ala Leu Ala Gly Val Leu Ala Ile L(eu)
5' AGCTT AC ATG AAG CTG CTT CTG GCC CTA GCA GGC GTC CTG GCC ATT C       3'
3'         AT G TAC TTC GAC GAA GAC CGG GAT CGT CCG CAG GAC CGG T       5'
   HindIII                                                        BglI
```

ADAPTOR 4

```
               27           30             35              40
5' AGCTT ACC Met Val Asp Leu Gly Pro Cys Trp Ala Gly Gly Leu Thr Ala
3'         AT GG ATG GTG GAC TTA GGA CCT TGC TGG GCT GGG GGT CTC ACT GCA 3'
   HindIII       TAC CAC CTG AAT CCT GGA ACG ACC CGA CCC CCA GAG TG      5'
                                                                    PstI
```

Double-stranded DNA adaptors were synthesized chemically a single-stranded oligonucleotides and hybridized prior to ligation (15).

Numbers above amino acids refer to the position in the preproMPO deduced amino acid sequence.

pNIV2705

This plasmid carries the sequences coding for a truncated form of preproMPO wherein 33 bp of the 5' coding region (aa 1 to 11) have been deleted. Instead of having the first ATG (Met1) as initiation codon, the cDNA module starts with the second in frame ATG (Met12). The construction proceeded as follows: a 611 bp BglI-AccIII DNA fragment derived from pNIV2703 was ligated, together with a synthetic 48 bp HindIII-BglI DNA piece coding for aa 12 to 24 (adaptor 3, Table I), to the large HindIII-AccIII fragment derived from pNIV2703. The resulting recombinant plasmid, pNIV2705, thus specifies a shortened MPO molecule of 734 amino acids.

pNIV2706

This plasmid carries the sequences coding for another truncated form of preproMPO wherein 78 bp of 5' coding sequences have been deleted (aa 1 to 26). Instead of having the first ATG (aa 1) as initiation codon, the cDNA module starts at the third in frame ATG (Met27). The construction consisted of ligating a 291 bp PstI-XbaI fragment derived from pNIV2703, together with a 50 bp synthetic HindIII-PstI DNA piece coding for aa 27 to 40 (adaptor 4, Table I), to the large HindIII-XbaI DNA fragment derived also from pNIV2703. The resulting recombinant plasmid, pNIV2706, thus encodes an N-terminally-truncated form of preproMPO (719 aa).

Transfection, Selection, Amplification and Expression in Mammalian Cells

Chinese hamster ovary cells DG44 dhfr⁻ (18) were maintained in alpha MEM medium, supplemented with ribo- and deoxyribonucleotides, 5% fetal calf serum and 2 mM L-glutamine. Transfections were performed by electroporation. In short, purified DNA of the three plasmids described above was digested with NotI to separate the pUC19 sequences from the eukaryotic fragment. The products of these digestions were used to transfect CHO cells using a Gene Pulser (Bio-Rad).

Approximately $10^7$ cells were preincubated on ice for 30 min. with 20 µg of DNA in 0.8 ml of 7 mM sodium phosphate buffer pH 7.4 containing 272 mM sucrose and 1 mM $MgCl_2$, and then electroporated at 600 V and 3 µFarads. After electroporation, cells were kept on ice for 10 min., added to 10 ml of culture medium and cultivated for 48 hours at an initial cell density of $2.5 \times 10^4$ per ml. The growth medium was then replaced by fresh medium supplemented with 400 µg/ml of G418, to select neomycin resistant cell lines. When appropriate, selections for resistance to methotrexate were performed as described for G418 selection. Selections were done in 96-well plates with 2,000–5,000 cells per well. Cell supernatants, and cells in some cases, were recovered to assay the production level and the enzymatic activity of secreted molecules.

Large Scale Cell Cultures

To produce milligram amounts of recMPO, the best producing clone was grown at 37° C. in alpha MEM medium supplemented with 5% FCS, 2 mM L-glutamine and 25 nM MTX, first in roller bottles and then in 6,000 $cm^2$ cell-factory units (NUNC). At confluence, culture medium was renewed with low serum concentration (1%) and the culture was maintained in this production medium for three to four weeks. Spent culture medium was collected at 3 to 4 day intervals, filtered through 0.45 μm membranes and stored at 4° C. until purification.

Purification of Extracellular recMPO from Spent Culture Medium

All purification steps were carried out at 4° C. Up to 2 liters of spent culture medium were passed through a Q-Sepharose Fast Flow Column (5×15 cm) equilibrated with 20 mM $KPO_4$ pH 7.5, at a flow rate of 400 ml/h. 90% of the enzymatic activity was recovered in the unadsorbed fraction. The flow-through fraction from the Q-Sepharose column was directly loaded onto a CM-Sepharose Fast Flow column (5×29 cm) equilibrated with the same buffer as above, supplemented with 100 mM NaCl. After extensive washing with the loading buffer, recMPO was eluted with 1200 ml of a linear NaCl gradient (100–500 mM) in the same buffer at a flow rate of 400 ml/h. 15 ml fractions were collected and those containing the MPO activity were pooled and applied onto a Chelating-Sepharose Fast Flow column (1.7×13 cm) saturated with $CuSO_4$ and equilibrated with 20 mM Tris-acetate pH 8.2 containing 500 mM NaCl. RecMPO was eluted, at a flow rate of 150 ml/h, with 200 ml of a linear pH gradient made of 20 mM Tris-acetate pH 8.2 and pH 3.9 in 500 mM NaCl. All the activity eluted in one peak at pH 5.5.

Gel Filtration Chromatography

About 200 activity units of natural and recombinant MPO, in 1 ml of PBS pH 7.5, were chromatographed on Sephacryl S200. The column (124×1.5 cm), equilibrated in 0.25M $KPO_4$ buffer, pH 7.5, was run at 10 ml/hour in the same buffer. 2 ml fractions were checked for absorbance at 280 nm and activity. A size calibration cure was obtained using β-amylase (Mr 200,000), alcohol dehydrogenase (Mr 150,000), bovine serum albumin (Mr 66,000), ovalbumin (Mr 45,000) and carbonic anhydrase (Mr 29,000) as standards.

Immunological Detection of recMPO

Recombinant protein levels in cell culture medium and in the course of the purification process were measured using an ELISA system according to the following protocol: 100 μl of a solution of rabbit antiserum to human MPO (diluted 1000-fold in PBS pH 7.5) was allowed to react in each well of 96-microwell trays (Nunc, Denmark) for one night at 4° C. The remaining adsorption sites were blocked by incubation with 150 μl of PBS pH 7.5 containing 0.1% Tween 80 and 1% BSA for 1 hour at 37° C. Plates were washed several times before 100 μl of diluted culture supernatants were added and allowed to react overnight at 4° C. with the adsorbed antibody. 100 μl of a solution of mouse antihuman MPO monoclonal antibody (diluted 1000-fold in PBS pH 7.5, 0.1% Tween 80, 1 BSA) was then allowed to react for 2 hours at 37° C. After washing, phosphatase alkaline-labelled immunoglobulins from a rabbit anti-mouse serum were used to reveal the mouse antibodies (100 μl per well of a solution of labelled immunoglobulins, diluted 1000 fold in Tris-Cl buffer pH 7.5 containing 0.15M NaCl, 0.1% Tween 80 and 1% BSA). After 90 min. incubation at 37° C., the wells were thoroughly washed. The bound enzyme was then revealed using a chromogenic substrate (150 μl of 1 mg/ml paranitrophenyl phosphate, in 1% diethanolamine, 0.5 mM $MgCl_2$, adjusted at pH 9.8 with 1N Hcl). The reaction was stopped by the addition of 40 μl of 3M NaOH and the absorbance was read at 410 nm (reference at 630 nm) in a microelisa automatic reader (Dynatech MR600).

Assay of Myeloperoxidase Activity

Enzyme activity was assayed using O-dianisidine as substrate, as described previously (19). One unit of the enzyme was defined as the amount catalyzing the increase of 1 unit in the absorbance at 470 nm in 1 min at room temperature. Enzyme activity was also determined with orthophenylenediamine (OPD) as substrate. For this, the reaction mixture consisted of 0.4 mg/ml OPD, 0.002% $H_2O_2$, 100 mM $NaPO_4$ pH 5, 150 mM NaCl in a total volume of 200 μl. The mixture was incubated for 5 min at room temperature and the reaction was stopped by the addition of 25 μl 2N $H_2SO_4$. The absorbance of the solution at 492 nm (reference at 620 nm) was then measured in a microplate reader (Dynatech) and the activity was expressed as the initial velocity of increase absorbance. A standard curve was obtained using recombinant and natural myeloperoxidases in the range of 125 to 1000 ng/ml.

SDS-PAGE and Western Blotting

SDS-PAGE was performed by the method of Laemmli (20). The minislab gel (0.75 mm thick, 50 mm long) consisted of a 7.5% or 10% separation polyacrylamide gel with a 3.5% stacking gel.

Immunoblotting of proteins on nitrocellulose sheets was performed essentially as described (21). Rabbit antibody raised against natural MPO (produced in the laboratory, according to ref. 22) was used to recognize the blotted MPO (dilution: 1:2000) and protein A conjugated to alkaline phosphatase as detection system (dilution: 1:2000). Standard proteins on the blot were stained with 0.3% Ponceau Red in 3% trichloracetic acid.

Amino Terminal Amino Acid Sequence Determination

Automated Edman degradation of the secreted recombinant MPO (about 100 μg protein) was performed in an Applied Biosystem sequencer model 477A equipped with a PTH-analyzer. The protein content was determined with bovine serum albumin as standard by the method of Bradford (23).

Glycosidase Digestion of Recombinant and Natural Human Myeloperoxidase

Recombinant and natural MPO from which carbohydrates were removed enzymatically to various extents were obtained as described below. Asialo-MPO was prepared by digesting MPO (260 μg) with 30 mU neuraminidase from Vibrio cholerae (SIGMA) for 3 h at 37° C. in 1.5 ml 100 mM sodium acetate pH 5 containing 10 mM $CaCl_2$. After incubation, the reaction mixture was dialyzed against 100 mM sodium phosphate pH 4.3. Then, exposed β-galactose residues in asialo-MPO were removed by the action of β-galactosidase. Asialo-MPO (65 μg) was incubated with 4.2 mU β-galactosidase from bovine testis (Boehringer) for 18 h at 37° C.

β-galactose and N-acetylglucosamine (β-Glc NAc residues were removed by double digestion of asialo-MPO (65 μg) with 4.2 mU β-galactosidase and 50 mU β-N-acetylglucosaminidase from *Aspergillus niger* (SIGMA) for 24 h at 37° C. Gal-β-(1–3)GalNAc residues were removed from the asialo-MPO (78 μg) after dialysis of the reaction mixture against 50 mM sodium phosphate pH 7.0, addition of 5 mU of endo-β-N-acetyl-galactosaminidase (O-glycosidase) from *Diplococcus pneumoniae* (Boehringer) and incubation for 3h30 at 37° C. The N-linked carbohydrates were removed by incubating MPO with glycopeptidase F from *Flavobacterium septicum* (Boehringer). First, MPO was denatured by overnight dialysis against 0.2% SDS at 4° C. and heating at 70° C. for 10 min. Then the reaction mixture was adjusted to a final concentration of 100 mM sodium phosphate pH 8 containing 20 mM EDTA, 0.5% Triton X-100, 1% β-mercaptoethanol and 0.16% SDS. MPO (50 μg) was incubated with 5U glycopeptidase F for 16 h at 37° C.

High mannose content was removed by incubating MPO (15 μg) with 150 mU endoglycosidase H from *S. plicatus* (Nenzyme, NEN Research Product, DUPONT) in 50 mM sodium phosphate pH 5.5 for 16 h at 37° C.

Fully deglycosylated MPO was prepared by successive digestions with neuraminidase, O-glycosidase and glycopeptidase F.

A control experiment for each digestion was done under the same conditions as described above except that glycosidases were omitted. All preparations were stored at 4° C. until used for analysis.

Carbohydrate Analysis

To confirm the completion of each glycosidase reaction, the preparations were analyzed by the ability of the residual exposed sugar to bind specific lectins.

Recombinant and natural MPO digested with glycosidases were transferred onto nitrocellulose filters after SDS-PAGE or directly dotted. The filters were treated using various lectins conjugated to alkaline phosphatase as described by the manufacturers. The following lectins were used: RCA Ricin (Ricinus Communis Agglutinin); PHA-E (Phaseolus Vulgaris Erythrolectin); WGA (Wheat Germ Agglutinin); GNA (Galanthus nivalis Agglutinin); SNA (Sambucus nigra Agglutinin); MAA (Maackia amurensis Agglutinin); PNA (Peanut Agglutinin).

TABLE II

Expression of recombinant MPO in CHO cell lines

| $G418^R$ clones (transfection with pNIV2703) | Production level (ng/ml/24 h) MTX (nM) | | | | Amplification factor |
|---|---|---|---|---|---|
| | 0 | 5 | 25 | 100 | |
| 17 | 441 | — | — | — | 0 |
| 17-7 | — | 782 | — | — | 1.78 |

TABLE II-continued

Expression of recombinant MPO in CHO cell lines

| $G418^R$ clones (transfection with pNIV2703) | Production level (ng/ml/24 h) MTX (nM) | | | | Amplification factor |
|---|---|---|---|---|---|
| | 0 | 5 | 25 | 100 | |
| 17-7-12 | — | — | — | 1968 | 4.46 |
| 24 | 480 | — | — | — | 0 |
| 24-1 | — | 958 | — | — | 2 |
| 24-1-4 | — | — | 2217 | — | 4.62 |
| 24-1-6 | — | — | 2429 | — | 5.06 |
| 24-1-7 | — | — | 2657 | — | 5.53 |

TABLE III

Purification of recombinant human myeloperoxidase from spent culture medium (CHO cell line 24.1.7).

| Fraction | Total protein mg | Activity units | Specific activity units/mg protein | Yield % | Prufication factor |
|---|---|---|---|---|---|
| spent culture medium | 850 | 6720 | 7.9 | 100 | — |
| Q-Sepharose | 320 | 6040 | 18.9 | 89.9 | 2.4 |
| CM-Sepharose | 10.5 | 5500 | 523.8 | 81.8 | 66.2 |
| Chelating Sepharose | 9.0 | 4860 | 537.0 | 72.3 | 67.8 |

2 liters of spent culture medium, collected after 3 days of culture in production medium (1% FCS), was used as starting material.

The specific activity was measured using orthophenylenediamine as substrate.

TABLE IV

Carbohydrate analysis of recombinant and natural MPO

Recombinant and natural MPO were treated with various glycosidases as described in Materials and Methods. After treatment, digested proteins were transferred onto nitrocellulose sheets and exposed carbohydrates were detected with sugar specific lectins conjugated to alkaline phosphatase.
MAA recognizes sialic acid linked α(2–3) to galactose;
RCS binds preferentially to oligosaccharides that end in galactose (Gal) but may also interact with N-acetylgalactosamine;
WGA binds to N-acetylglucosamine (GlcNAc), preferentially to dimers and to a lesser degree to sialic acid (NeuNAc);
GNA recognizes terminal mannose, α(1–3), α(1–6) or α(1–2) linked to mannose and is suitable for identifying "high-mannose" N-glycan chains;
PHA-E binds to complex oligosaccharides having the trisaccharide Galβ(1–4) GlcNAcβ(1–2) Man linked β(1–6) to mannose;
SNA recognizes sialic acid linked α(2–6) to galactose;
PNA recognizes the core disaccharide galactose β(1–3) N-acetylgalactosamine and is thus suitable for identifying O-glycosidically linked carbohydrate chains. If the disaccharide is substituted, it is necessary to split off the substitute group first, e.g. sialic acid, with the aid of neuraminidase;
R and N indicate recMPO and natural MPO respectively;
+ and − refer to binding and no binding of the sugar-specific lectin; and
nd: not done.

| Glycosidase treatment | Lecithin | | | | | | | | | | | | | |
|---|---|---|---|---|---|---|---|---|---|---|---|---|---|---|
| | MAA | | RCA | | WGA | | GNA | | PHA-E | | SNA | | PNA | |
| | R | N | R | N | R | N | R | N | R | N | R | N | R | N |
| untreated | + | + | + | + | + | + | + | + | + | + | − | − | − | − |
| sialidase | − | − | + | + | + | + | + | + | + | + | − | − | + | + |
| sialidase/ β-galactosidase | − | − | − | − | + | + | + | + | + | + | − | − | − | − |
| sialidase/ β-galactosidase/ | − | − | − | − | + | + | + | + | + | + | − | − | | |

TABLE IV-continued

| Carbohydrate analysis of recombinant and natural MPO | | | | | | | | | | | | | | |
|---|---|---|---|---|---|---|---|---|---|---|---|---|---|---|
| β-N-acetyl-glucosaminidase glycopeptidase F | — | nd | — | nd | — | nd | — | nd | — | nd | — | nd | — | nd |
| fully deglycosylated (sialidase, N-glycosidase F, O-glycosidase) | — | nd | — | nd | — | nd | — | nd | — | nd | — | nd | — | nd |

References Cited in Example 2

1. Klebanoff, S. J. (1988) *J. Bacteriol.* 95, 2131–2138.
2. Henderson, W. R. and Klebanoff, S. J. (1988) *J. Biol. Chem.* 258, 13522–13527.
3. Matheson, N. R., Wong, P. S. and Travis, J. (1979) *Biochem. Biophys. Res. Commun.* 88, 402–409.
4. Bakkenist, A. R. J., Wever, R., Vulsma, T., Plat, H. and Van Gelder, B. F. (1978) *Biochem. Biophys. Acta* 524, 45–54.
5. Andrew, P. C. and Krinsky, N. I. (1981) *J. Biol. Chem.* 256, 4211–4218.
6. Atkin, C. L., Andersen, M. R. and Eyre, H. J. (1982) *Arch. Biochem. Biophys.* 214, 284–292.
7. Yamada, Y., Mori, M. and Sugimura, T. (1981) *Biochemistry* 20, 766–771.
8. Hur, S. J., Toda, H. and Yamada, M. (1989) *J. Biol. Chem.* 264, 8542–8548.
9. Morishita, K., Kubota, N., Asana, S., Kaziro, Y. and Nagata, S. (1987) *J. Biol. Chem.* 262, 3844–3851.
10. Johnson, K. R., Nauseef, W. M., Care, A., Wheelock, M. J., Shane, S., Hudson, S., Koeffler, H. P., Selsted, M., Miller, C. and Rovera, G. (1987) *Nucleic Acids Res.* 15, 2013–2028.
11. Hashinaka, K., Nishio, C., Hur, S. J., Sakyama, F., Tsunasawa, S. and Yamada, M. (1988) *Biochemistry* 27, 5906–5914.
12. Yamada, M., Hur, S. J. and Toda, H. (1990) *Biochem. Biophys. Res. Commun.* 166, 852–859.
13. Taylor, K. L., Guzman, G. S., Burgess, C. A. and Kinkade, J. M. Jr. (1990) *Biochemistry* 29, 1533–1539.
14. Connors, R. W., Sweet, R. W., Noveral, J. P., Pfarr, D. S., Trill, J. J., Shebuski, R. J., Berkowitz, B. A., Williams, D., Franklin, S. and Reff, M. E. (1988) *DNA* 7, 651–660.
15. Maniatis, T., Fritsch, E. F. and Sambrook, J. (1982) *Molecular Cloning: a laboratory manual.* Cold Spring Harbor Laboratory, Cold Spring Harbor, N.Y.
16. Matteucci, M. D. and Caruthers, M. H. (1981) *J. Am. Chem. Soc.* 103, 3185–3191.
17. Sanger, F., Nicklen, S. and Coulson, A. R. (1977) *Proc. Natl. Acad. Sci. U.S.A.* 74, 5463–5467.
18. Urlaub, G. and Chasin, L. A. (1980) *Proc. Natl. Acad. Sci. U.S.A.* 77, 4216–4220.
19. Krawisz, J. E., Sharon, P. and Stenson, W. F. (1984) *Gastroenterology* 87, 1344–1350.
20. Laemmli, U. K. (1970) *Nature* 227, 680–685.
21. Towbin, H., Staehelin, T. and Gordon, J. (1979) *Proc. Natl. Acad. Sci. U.S.A.* 76, 4350–4354.
22. Olsson., I, Olofsson, T. and Odeberg, H. (1972) *Scand. J. Haematol.* 9, 483–491.
23. Bradford, M. M. (1976) *Anal. Biochem.* 72, 248–254.
24. Kozak, M. (1986) *Cell* 44, 283–292.
25. Bakkenist, A. R. J., De Boer, J. E. G., Plat, H. and Wever, R. (1980) *Biochem. Biophys. Acta* 613, 337–348.
26. Schwarz, R. T. and Datema, R. (1980) *TIBS* 5, 65–67.
27. Hasilik, A., Pohlmann, R., Olsen, R. L. and Von Figura, K. (1984) *EMBO J.* 3, 2671–2676.
28. Tarentino, A. L., Gomez, C. M. and Plummer, T. H. (1985) *Biochemistry* 24, 4665–4671.
29. Tarentino, A. L., Plummer, T. H. and Maley, F. (1974) *J. Biol. Chem.* 249, 818–824.
30. Umemoto, J., Bhavanandan, V. P. and Davidson, E. A. (1977) *J. Biol. Chem* 252., 8609–8614.
31. Olsen, R. L. and Little, C. (1983) *Biochem. J.* 209, 781–787.
32. Matheson, N. R., Wong, P. S. and Travis J. (1981) *Biochemistry* 20, 325–330.
33. Pember, S. O., Shapiro, R. and Kinkade, J. M. Jr. (1983) *Arch. Biochem. Biophys.* 221, 391–403.
34. Miyasaki, K. T., Wilson, M. E., Cohen, E., Jones, P. C. and Genco, R. J. (1986) *Arch. Biochem. Biophys.* 246, 751–764.
35. Yamada, M. (1982) *J. Biol. Chem.* 257, 5980–5982.
36. Akin, D. T. and Kinkade, J. M. Jr. (1986) *J. Biol. Chem.* 261, 8370–8375.
37. Nauseef W. M. and Clark, R. A. (1986) *Blood* 68, 442–449.
38. Akin, D. T., Parmley, R. T. and Kinkade, J. M. Jr. (1987) *Arch. Biochem. Biophys.* 257, 451–463.
39. Klebanoff, S. J. and Hamon, C. B. (1972) *J. Reticuloendothel. Soc.* 12, 170–196.
40. Wright, C. and Nelson, R. D. (1985) *Infect. Immun.* 47, 363–365.
41. Rojas-Espinosa, O. (1988) *J. Leuko. Biol.* 43, 468–470.
42. Humphreys, J. M., Davies, B., Hart, A. and Edwards, S. W. (1989) *J. Gen. Microbiol.* 135, 1187–1193.

Example 3

Therapeutic Application of hMPO

Role of Leukocytic Myeloperoxidase

Our body's defense against foreign microorganisms is effected by the white cells or leukocytes, including the lymphocytes which produce antibodies, the macrophages, eosinophils and neutrophils (or polymorphonuclear cells) which destroy the foreign microorganism by phagocytosis. During the latter, the neutrophils generate highly toxic and bactericidal oxygenated species: the superoxide anion, hydrogen peroxide, the hydroxyl radical and singlet oxygen.

The bactericidal action of hydrogen peroxide ($H_2O_2$) is increased one thousand-fold by myeloperoxidase (MPO), an enzyme localized in the azurophil (or primary) granules of neutrophils. In effect, this enzyme catalyzes, in the presence of $H_2O_2$, the oxidation of chloride ion ($Cl^-$ to generate hypochlorous acid (HOCl) (1) which has bactericidal properties.

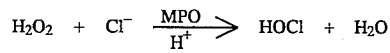

$$H_2O_2 + Cl^- \xrightarrow[H^+]{MPO} HOCl + H_2O$$

Monocytes, which are macrophage precursors, process a mechanism of antimicrobial activity similar to neutrophils, but they produce only small amounts of $H_2O_2$ and, furthermore, they possess approximately one third the amount of myeloperoxidase possessed by neutrophils (2). Moreover, in vitro experiments have shown that, during their maturation to macrophages, they completely lose their myeloperoxidase content, which also results in a decrease in the antibacterial activity (3). Thus, freshly isolated monocytes have a 90% cytotoxicity with respect to ingested *Toxoplasma gondii*, while macrophages (10 days of culture) display, at this stage of development, only 12% cytotoxicity.

However, several studies have shown that macrophages could phagocytose neutrophil cell debris (4, 5) and could thereby acquire myeloperoxidase activity, resulting in an increase in the toxicity of the small amount of hydrogen peroxide produced by the macrophages. Other studies have underlined the extent of the increase in the peroxidase activity of macrophages since, if *T. gondii* cells are incubated beforehand with horse eosinophil peroxidase, the macrophages then recover a 90% cytotoxicity, equivalent to that of monocytes (3, 6). The same observations have been made with *S. aureus* (7), *T. cruzi* (8) or tumor cells (9).

MATERIALS AND METHODS

Purification of Human Monocytes 50 ml of blood of a normal subject are drawn onto Calciparine (0.3 ml containing 25,000 U/ml) and then diluted two-fold with 0.01M PBS buffer pH 7.2. 35 ml of diluted blood are then deposited on a density gradient consisting of 15 ml Ficoll-Paque (Pharmacia).

After centrifugation at room temperature at 1,800 rpm for 30 minutes, the lymphocytes and monocytes located at the gradient interface are recovered and stored on ice. The cells are then washed once with PBS buffer and thereafter centrifuged at 2,000 rpm for 10 minutes at 4° C. The operation is repeated twice more and the cells are then cultured.

Culturing of Human Monocytes

The monocytes are purified by adhesion to glass. In cups 2.5 cm in diameter (Limbro), the cells are brought into contact with 1 ml of MEM culture medium containing 10% of human serum. After incubation at 37° C. for 2 hours in a 5% $CO_2$ atmosphere, the non-adherent cells (lymphocytes) are removed by drawing off the supernatant. The adherent monocytes are placed in contact again with 1 ml of MEM also containing 10% of human serum, and then left in culture.

I. Demonstration by Microscopy of the Incorporation of Myeloperoxidase into Monocytes I.1 Method The monocytes are brought into contact with 980 ng/ml of semi-purified human leukocytic myeloperoxidase. After 4 hours' incubation at 37° C., the MEM culture medium is removed and the monocytes are washed carefully with PBS buffer. The monocytes are then detached by vigorous agitation with 1 ml of PBS buffer and thereafter centrifuged so as to form a spot on a microscope slide.

The slides are fixed with ethanol/formaldehyde solution (9:1) at room temperature, then washed with water and thereafter air dried. The peroxidase activity of the monocytes is demonstrated by depositing a few drops of a mixture of 1% benzidine (30 ml), ten-fold diluted 4% sodium nitroprusside (0.3 ml) and 0.3 ml of 80-fold diluted $H_2O_2$ on the slide.

After 2 minutes' contact at room temperature, the slides are washed copiously with water and then air dried.

In a final step, the slides are stained with Giemsa to demonstrate the cells.

The slides are then examined under a microscope.

I.2 Results

Control monocytes display only very little positive reaction with benzidine.

Only a few monocytes develop a slightly brownish staining, thereby clearly demonstrating that myeloperoxidase is present in only small amounts in these cells.

In contrast, monocytes cultured for 24 hours and brought into contact with myeloperoxidase react positively and very distinctly with benzidine. These first results confirm an incorporation of myeloperoxidase by simple phagocytosis into monocytes.

II. Demonstration by Radioimmunoassay of the Incorporation of Myeloperoxidase by Monocytes II.1 Method After adherent monocytes have been brought into contact with 1 ml of MOM buffer containing semi-purified myeloperoxidase, or neutrophil debris obtained by sonication (the protocol of four experiments is described in detail in the results), the supernatant is recovered and then centrifuged at 2,000 rpm for 10 minutes in order to recover monocytes which may possibly have become detached (pellet 1).

The adherent monocytes are detached by efficient agitation with 1 ml of PBS buffer. They are added to pellet 1 and then centrifuged at 2,000 rpm for 10 minutes at 4° C. After three washes with PBS buffer, the cells are counted and then diluted so as to obtain 3 million monocytes per ml.

The myeloperoxidase of the monocytes is solubilized by treating the cells with cetyltrimethylammoniumbromide (0.01%) and by two successive freezings.

After return to room temperature, 100 µl of the medium are withdrawn for quantification of the enzyme according to a specific radioimmunoassay technique (10).

II.2 Results

Experiment 1

Three million monocytes, cultured for 24 hours, are brought into contact for 2 hours with 1 ml of MEM culture medium containing:

a) MPO 1=semi-purified myeloperoxidase at a concentration of 980 ng/ml b) MPO 2=50 µl of a concentrated suspension of sonicated neutrophil debris.

| 1 | myeloperoxidase ng/ml | % increase in the intracellular content |
|---|---|---|
| Monocytes 24 h (3 million) | 80 | |
| Monocytes 24 h + MPO 1 (2 hours' incubation) | 88 | 1.1 |
| Monocytes 24 h + MPO 2 (2 hours' incubation) | 358 | 447 |

The base-line level of monocytes which have not been brought into contact with monocytes which have not been brought into contact with myeloperoxidase is 80 ng/ml. After 2 hours' incubation with semi-purified myeloperoxidase, the intracellular myeloperoxidase level of the monocytes remains unchanged. In contrast, a strong increase (447% of the base-line level) in the intracellular myeloperoxidase concentration is observed when the monocytes are brought into contact with neutrophil debris. The latter observation shows that monocytes are indeed capable of phagocytosing neutrophil debris.

Experiment 2

The conditions are identical to those in Experiment 1, except that the incubation time is 4 hours. In this instance, a marked increase (440%) is noted in the intracellular myeloperoxidase content of monocytes which have been brought into contact with the enzyme. Similarly, the neutrophil debris is to phagocytose even better than in the previous experiment, since there is a 2,070% increase in the intracellular myeloperoxidase content.

| 1 | myeloperoxidase ng/ml | % increase in the intracellular content |
|---|---|---|
| Monocytes 24 h (3 million) | 54 | |
| Monocytes 24 h + MPO 1 (4 hours' incubation) | 238 | 440 |
| Monocytes 24 h + MPO 2 (4 hours' incubation) | 1,120 | 2,070 |

Experiment 3

The table below shows that monocytes cultured for 48 hours incorporate myeloperoxidase or neutrophil debris better after 2 hours' incubation than monocytes cultured for 24 hours.

| 3 | myeloperoxidase ng/ml | % increase in the intracellular content |
|---|---|---|
| Monocytes 48 h (3 million) | 102 | |
| Monocytes 48 h + MPO 1 (2 hours' incubation) | 204 | 220 |
| Monocytes 48 h + MPO 2 (2 hours' incubation) | 788 | 772 |

Experiment 4

Monocytes cultured for 24 hours are, in this instance, brought into contact for 2 hours and 6 hours with 1 ml of culture buffer containing 3,920 ng/ml of semi-purified myeloperoxidase (MPO3).

| 4 | myeloperoxidase ng/ml | U/ml | % increase in the cell content |
|---|---|---|---|
| Monocytes 24 h (3 million) | 90 | 0.6 | |
| Monocytes 24 h + MPO 3 (2 hours' incubation) | 136 | 0.86 | 151 |
| Monocytes 24 h + MPO 3 (6 hours' incubation) | 324 | 1.3 | 360 |

After being brought into contact with the enzyme for 2 hours, the monocytes increase their intracellular content by 151%, whereas, in Experiment 1, this content has remained unchanged. The increase is still more marked after being brought into contact for 6 hours. In this experiment, the enzymatic activity of the myeloperoxidase, determined by the oxidation of o-dianisidine in the presence of $H_2O_2$ was also measured. The base-line level of 0.6 U/ml increases as the contact time increases (value doubled after 6 hours). This finding is proof that exogenous myeloperoxidase incorporated into monocytes indeed remains enzymatically active.

III. Cytotoxicity of Monocytes which Incorporated Myeloperoxidase with Respect to Schistosomula III.1 Method The schistosomula are isolated from cercariae by an artificial technique (filtration through a piece of mouse skin). The following experimental protocol was adopted: 24-hour monocytes are incubated for 2 hours with myeloperoxidase and then washed carefully with MEM culture medium. The monocytes, treated or otherwise with myeloperoxidase, are then incubated for 6 hours with serum of a subject suffering from bilharziosis (10%) or with a serum of a health subject (10%) which serves as a control (inherent effect of the serum). Schistosomula, treated beforehand or otherwise with myeloperoxidase, are then added to the culture medium. After 16 hours, the live and dead schistosomula are counted and a % cytotoxicity of the monocytes is thereby determined.

| Monocytes: 100 to 200,000 cells cultured for 24 hours | | | |
|---|---|---|---|
| 0 | 2 h | 8 h | 24 h |
| MPO 1 | healthy serum or | schistosomula | reading |
| MPO 2 | bilharziosis serum | | |

Experiment 5

These results show that the cytotoxicity of monocytes which have previously incorporated MPO 1 or MPO 2 with respect to schistosomula in the presence of bilharziosis serum is increased by 50% compared to control monocytes. The true percentage cytotoxicity is obtained by subtracting the value obtained with health serum (inherent effect of the serum) from the value obtained with the bilharziosis serum.

| | % cytotoxicity of monocytes | | |
|---|---|---|---|
| 5 | without MPO | + MPO 1 | + MPO 2 |
| bilharziosis serum | 42.5 ± 5 | 70.5 ± 10.5 | 71.5 ± 3 |
| healthy serum, 10% | 19 ± 0 | 26 ± 1.4 | 25 ± 5 |
| true % cytotoxicity | 23.5 | 44.5 | 46.5 |

Experiment 6

In this experiment, a comparison was made between the cytotoxicity of monocytes which had or had not incorporated myeloperoxidase with respect to normal schistosomula (stimulus 1) and schistosomula which had been brought into contact beforehand for 2 hours with 980 ng/ml of myeloperoxidase (stimulus 2).

| | % cytotoxicity of monocytes | | | |
|---|---|---|---|---|
| | without MPO | | + MPO 1 | |
| 6 | stimulus 1 | stimulus 2 | stimulus 1 | stimulus 2 |
| bilharziosis serum, 10% | 42.5 ± 5 | 62.5 ± 2 | 70.5 ± 10.5 | 99 |
| healthy serum, 10% | 19 ± 0 | 22 ± 4 | 26 ± 4.1 | 35.5 ± 2 |
| true % cytotoxicity | 23.5 | 40.5 | 44.5 | 64 |

Monocytes not treated with myeloperoxidase have a cytotoxicity which rises from 23.5 to 40.5% when they are brought into contact with schistosomula coated with myeloperoxidase.

Although the model is different (in this case, the monocyte does not kill the schistosomulum by phagocytosis but by simple adhesion to it), this observation is in agreement with previous work showing that the cytotoxicity of macrophages is increased when the infectious organism (*T. gondii*) phagocytosed is coated with a peroxidase (3,6).

The combination of monocytes which have incorporated myeloperoxidase with schistosomula coated with the enzyme enables a very high cytotoxicity (64%) to be obtained.

Conclusions

It was only shown in the literature that monocytes can acquire an accompanied peroxidase, that is to say a peroxidase associated with a support which is a microorganism, and can thereby undergo an increase in their cytotoxicity with respect to a whole series of infectious organisms. In these experiments, it should, in effect, be noted that the myeloperoxidase was first linked to the infectious organism, which was then ingested by the monocyte or macrophage.

According to the invention, human granulocytic myeloperoxidase has been used, and it has been discovered that:

1) myeloperoxidase can be phagocytosed directly without the intervention of an activator by the monocyte, 2) the ingested enzyme remains enzymatically highly active, as shown by the results on cytotoxicity with respect to schistosomula.

These observations indicate that exogenous myeloperoxidase administered to the body will be taken up by human monocytes or macrophages, and can consequently be used as a therapeutic means in patients suffering from deficiencies, hereditary (agranulocytosis) or acquired (AIDS).

REFERENCES

1. Zgliczynski J. M., Stelmaseynska D., Domanski J. and Cstrowski W. "Chloramines as intermediates of oxidative reaction of amino acids by myeloperoxidase" *Biochim. Biophys. Acta* 1971, 235: 419–424.
2. Bos, A., Wever, R. and Roos, D. "Characterization and quantification of the peroxidase in human monocytes" *Biochim. Biophys. Acta* 1978, 525: 37–44.
3. Locksley R. M., Nelson C. S., Fankhauser J. E. and Klebanoff S. J. "Loss of granule myeloperoxidase during in vitro culture of human monocytes correlates with decay in antiprotozoa activity" *Am. J. Trop. Med. Hyg.* 1987, 36(3):541–548.
4. Hoifets, L., Katsuyuki, I. and Mayer, G. "Expression of peroxidase-dependent iodination by macrophages ingesting neutrophils debris" *J. Reticuloendothel Soc.* 1980, 28(3):391–404.
5. Atwal, O. "Cytoenzymological behavior of peritoneal exudate cells of rat in vivo" *J. Reticuloendothel Soc.* 1971, 10:163–172
6. Locksley, R. M., Wilson, C. B. and Klebanoff, S. J. "Role of endogenous and acquired peroxidase in the toxoplasmacidal activity of murine and human mononuclear phagocytes" *J. Clin. Invost.* 1982, 69:1099–1111.
7. Ramsey, P. G., Martin, T., Chi, E. and Klebanoff, S. J. "Arming of mononuclear phagocytes by eosinophil peroxidase bound to staphylococcus aureus" *J. Immunol.* 1982, 128:415–420.
8. Nogueira, N. H., Klebanoff, S. J. and Cohn, Z. A. "Teruzi sensitization to macrophage killing by eosinophil peroxidase" *J. Immunol.* 1982, 128: 1705–1708.
9. Nathan, C. F. and Klebanoff, S. J. "Augmentation of spontaneous macrophage-mediated cytolysis of eosinophil peroxidase" *J. Exp. Med.* 1982, 155:1291–1308.
10. Deby-Dupont, G., Pincemail, J., Thirion, A. and Deby, C. "A radioimmunoassay for polymorphonuclear leucocytes myeloperoxidase: preliminary results" *Arch. Int. Physiol. Biochim.* 1987 (in press).

We claim:

1. A substantially pure recombinant human myeloperoxidase heme-containing precursor, comprising a glycoprotein of 84 KD with the amino acid sequence coded for by the nucleotide sequence from 145 to 2235 corresponding to codons 49 to 745 in phase after the first methionine codon in FIG. 1 produced by culturing prokaryotic or eukaryotic cells transformed by a vector for the expression of human myeloperoxidase precursor in said cells.

2. Substantially pure recombinant human myeloperoxidase having the amino acid sequence represented in FIG. 15.

3. The substantially pure recombinant human myeloperoxidase heme-containing precursor according to claim 1, which is produced by a culture of higher eukaryotic cells selected from the group consisting of insect and mammalian cells.

4. A medicinal product, comprising substantially pure recombinant human myeloperoxidase heme-containing precursor, comprising a glycoprotein of 84 KD with the amino acid sequence coded for by the nucleotide sequence from 145 to 2235 corresponding to codons 49 to 745 in phase after the first methionine codon in FIG. 1 produced by culturing prokaryotic or eukaryotic cells transformed by a vector for the expression of human myeloperoxidase precursor in said cells.

5. The medicinal product according to claim 4, wherein said substantially pure recombinant human myeloperoxidase has the amino acid sequence represented in FIG. 15.

6. The medicinal product according to claim 4, wherein said substantially pure recombinant human myeloperoxidase heme-containing precursor is produced by a culture of higher eukaryotic cells selected from the group consisting of insect and mammalian cells.

7. A medicinal product comprising substantially pure recombinant human myeloperoxidase heme-containing precursor, comprising a glycoprotein of 84 KD with the amino acid sequence coded for by the nucleotide sequence from 145 to 2235 corresponding to codons 49 to 745 in phase after the first methionine codon in FIG. 1, produced by culturing mammalian cells transfected by a vector, the vector including a sequence selected from the group consisting of the cDNA for human myeloperoxidase or the coding sequence of the recombinant human myeloperoxidase consisting in the DNA sequence in FIG. 1 starting either at the first ATG coded for by nucleotides 1–3, at the second ATG which is coded for by nucleotides 34–36 and corresponds to the codon in position 12, or the third ATG which is coded for by nucleotides 79–81 and corresponds to the codon in position 27, these two last ATG being in phase with the first ATG, in FIG. 1.

8. A medicinal product for the treatment of immunodeficiencies caused by burns or irradiation, comprising:

substantially pure recombinant human myeloperoxidase heme-containing precursor, comprising a glycoprotein of 84 KD with the amino acid sequence coded for by the nucleotide sequence from 145 to 2235 corresponding to codons 49 to 745 in phase after the first methionine codon in FIG. 1 produced by culturing prokaryotic or eukaryotic cells transformed by a vector for the expression of human myeloperoxidase precursor in said cells.

9. The medicinal product according to claim 8, wherein said substantially pure recombinant human myeloperoxidase has the amino acid sequence represented in FIG. 15.

10. The medicinal product according to claim 8, wherein said substantially pure recombinant human myeloperoxidase heme-containing precursor is produced by a culture of higher eukaryotic cells selected from the group consisting of insect and mammalian cells.

11. A medicinal product for the treatment of immunodeficiencies caused by burns or irradiation, comprising:

substantially pure recombinant human myeloperoxidase heme-containing precursor, comprising a glycoprotein of 84 KD with the amine acid sequence coded for by the nucleotide sequence from 145 to 2235 corresponding to codons 49 to 744 in phase after the first methionine codon in FIG. 1, produced by culturing mammalian cells transfected by a vector, the vector including a sequence selected from the group consisting of the cDNA for human myeloperoxidase or the coding sequence of the recombinant human myeloperoxidase consisting in the DNA sequence in FIG. 1 starting either at the first ATG coded for by nucleotides 1–3, at the second ATG which is coded for by nucleotides 34–36 and corresponds to the codon in position 12, or the third ATG which is coded for by nucleotides 79–81 and corresponds to the codon in position 27, these two last ATG being in phase with the first ATG, in FIG. 1.

12. A medicinal product comprising a conjugated substantially pure recombinant human myeloperoxidase, wherein said myeloperoxidase is conjugated by covalent coupling or complexing to a transporting agent possessing an affinity for macrophages.

13. The medicinal product according to claim 12, wherein the transporting agent is selected from the group consisting of mannosylated human albumin, an antibody directed towards receptors present on macrophages, an antibody fragment directed towards receptors present on macrophages, and an Fc constant portion directed towards receptors present on macrophages.

* * * * *